United States Patent
Uehara et al.

(10) Patent No.: US 6,455,535 B1
(45) Date of Patent: Sep. 24, 2002

(54) SUBSTITUTED AMINOQUINAZOLINONE (THIONE) DERIVATIVES OR SALTS THEREOF, INTERMEDIATES THEREOF, AND PEST CONTROLLERS AND A METHOD FOR USING THE SAME

(75) Inventors: Masahiro Uehara, Sakai; Masamitsu Watanabe, Kawachinagano; Masayuki Kimura, Kawachinagano; Masayuki Morimoto, Kawachinagano; Masanori Yoshida, Hashimoto, all of (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/702,757

(22) Filed: Nov. 1, 2000

(30) Foreign Application Priority Data

Nov. 2, 1999 (JP) ............................................ 11-312297
Mar. 30, 2000 (JP) ........................................ 2000-094493

(51) Int. Cl.[7] ........................ C07D 401/12; A01N 43/54
(52) U.S. Cl. ........................................ 514/259; 544/284
(58) Field of Search ............................ 544/284; 514/259

(56) References Cited

U.S. PATENT DOCUMENTS 5,714,492 A * 2/1998 Uehara et al. ............... 514/259

FOREIGN PATENT DOCUMENTS

EP           0 735 035           10/1996

* cited by examiner

*Primary Examiner*—Deepak R. Rao
(74) *Attorney, Agent, or Firm*—Paul E. White, Jr.; Manelli Denison & Selter PLLC

(57) ABSTRACT

The present invention relates to substituted aminoquinazolinone (thione) derivatives or salts thereof, intermediates thereof for preparing the same, pest controller compositions and methods for using the same, where in particular, the compounds of the present invention, having the substituents in the phenyl group which belongs to the quinazolinone ring, possess superior insecticidal effects at low dosage and more particularly, the novel aminoquinazolinone derivatives having bromine atom, iodine atom, perfluoroalkyl group, perfluoroalkoxy group or the like in the quinazoline ring possess excellent insecticidal activities.

3 Claims, No Drawings

SUBSTITUTED AMINOQUINAZOLINONE (THIONE) DERIVATIVES OR SALTS THEREOF, INTERMEDIATES THEREOF, AND PEST CONTROLLERS AND A METHOD FOR USING THE SAME

BACKGROUND OF THE INVENTION

1. Field of the Invention

The present invention relates to substituted aminoquinazolinone (thione) derivatives or salts thereof, intermediates thereof for preparing the same, pest controllers and a method for using the same.

2. Related Art

Japanese Patent Unexamined Publication, JP-A-8-325239 discloses that aminoquinazolinone derivatives are useful as pest controllers.

SUMMARY OF THE INVENTION

As a consequence of investigation earnestly conducted for finding a novel pest controller, the present inventors found that compounds of the present invention, having the substituents in the phenyl group which is belonging to the quinazolinone ring, possess the same or better insecticidal effects at low dosage as compared with compounds of Examples disclosed in the above-mentioned JP-A-8-325239. Particularly the compounds of the present invention possess sufficient insecticidal effects against whiteflies under consideration in the agricultural and horticultural fields, consequently the present inventors have accomplished the present invention.

The substituted aminoquinazolinone (thione) derivatives or salts thereof represented by the general formula (I) and the compounds represented by the general formula (II) which are intermediates for preparing the derivatives of the general formula (I) are novel compounds which have not been known in any prior art literature. Furthermore, pest controllers containing, as the active ingredient, the substituted aminoquinazolinone (thione) derivative represented by the general formula (I) or salts thereof possess excellent insecticidal effects against various insects at low dosage as compared with conventional pest controllers.

The present inventors have earnestly conducted investigation on the aminoquinazolinone (thione) derivatives for developing a novel pest controller having expanded inscetical spectrum. Finally, the inventors have found the fact that novel aminoquinazolinone derivatives having bromine atom, iodine atom, perfluoroalkyl group, perfluoroalkoxy group or the like in the quinazoline ring possess quite excellent insecticidal activities as pest controllers.

DETAILED DESCRIPTION OF THE INVENTION

The present invention relates to substituted aminoquinazolinone (thione) derivatives represented by the general formula (I), or salts thereof:

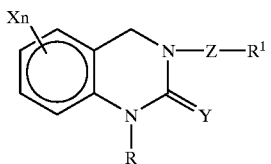

[where R is a hydrogen atom; a hydroxyl group; a formyl group; a $(C_{1-12})$alkyl group; a halo$(C_{1-6})$alkyl group; a hydroxy$(C_{1-6})$alkyl group; a $(C_{2-6})$alkenyl group; a $(C_{2-6})$-alkynyl group; a $(C_{1-6})$alkoxy group; a halo$(C_{1-6})$alkoxy group; a $(C_{1-6})$alkoxy$(C_{1-3})$alkyl group; a $(C_{1-6})$alkoxy$(C_{1-3})$alkoxy$(C_{1-3})$alkyl group; a $(C_{1-6})$alkylthio group; a halo$(C_{1-6})$alkylthio group; a $(C_{1-6})$alkylsulfinyl group; a $(C_{1-6})$alkylsulfonyl group; a $(C_{1-6})$alkylthio$(C_{1-3})$alkyl group; a di$(C_{1-6})$alkoxy$(C_{1-3})$alkyl group in which the $(C_{1-6})$alkoxy groups may be the same or different; an unsubstituted amino$(C_{1-6})$alkyl group; a substituted amino$(C_{1-6})$alkyl group having one or two substituents which may be the same or different and are selected from the group consisting of $(C_{1-6})$alkyl groups, halo$(C_{1-6})$alkyl groups, $(C_{2-6})$alkenyl groups and $(C_{2-6})$alkynyl groups; a cyano$(C_{1-6})$alkyl group; a $(C_{1-6})$alkylcarbonyl group; a $(C_{1-6})$alkoxycarbonyl group; a hydroxycarbonyl-$(C_{1-3})$alkyl group; a $(C_{1-6})$alkoxycarbonyl$(C_{1-3})$alkyl group; an unsubstituted aminocarbonyl group; a substituted aminocarbonyl group having one or two substituents which may be the same or different and are selected from the group consisting of $(C_{1-6})$alkyl groups, $(C_{2-6})$alkenyl groups and $(C_{2-6})$alkynyl groups; a $(C_{3-6})$-cycloalkyl$(C_{1-3})$alkyl group; an unsubstituted phenyl$(C_{1-3})$alkyl group; a substituted phenyl$(C_{1-3})$alkyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylcarbonyl group; a substituted phenylcarbonyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenylthio group; a substituted phenylthio group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyl-sulfonyl group; a substituted phenylsulfonyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyl$(C_{1-6})$alkylsulfonyl group; a substituted phenyl$(C_{1-6})$alkylsulfonyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyloxycarbonyl group; a substituted phenyloxycarbonyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$-alkoxy groups, $(C_{1-6})$alkylthio groups and halo$(C_{1-6})$-alkylthio groups; an unsubstituted phenyloxy$(C_{1-3})$alkyl group, a substituted phenyloxy$(C_{1-3})$alkyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyl$(C_{2-6})$-alkenyl group, a substituted phenyl$(C_{2-6})$alkenyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups; an unsubstituted phenyl$(C_{2-6})$alkynyl group; a substituted phenyl$(C_{2-6})$alkynyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups; an unsubstituted phenyl$(C_{2-4})$alkynyl$(C_{1-3})$alkyl group; a substituted phenyl$(C_{2-4})$alkynyl$(C_{1-3})$alkyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups and $(C_{1-2})$alkylenedioxy groups; a 1,3-dioxolan-2-yl$(C_{1-3})$alkyl group; or a phthalimido$(C_{1-6})$alkyl group, $R^1$ is a 5- or 6-membered heterocyclic ring having 1 to 3 heteroatoms which may be the same or different and are selected from the group consisting of oxygen atom, sulfur atom and nitrogen atom, said heterocyclic ring may have 1 to 5 substituents which may be the same or different and are selected from the group consisting of halogen atoms, cyano groups, $(C_{1-6})$alkyl groups, halo$(C_{1-6})$alkyl groups and $(C_{1-6})$alkoxy groups, and the nitrogen atom in the heterocyclic ring may form an N-oxide group, Y is an oxygen atom or a sulfur atom, Z is

—N=C(R$^2$)—

(wherein $R^2$ is a hydrogen atom, a $(C_{1-6})$alkyl group or a halo$(C_{1-6})$alkyl group), or

—N(R$^3$)—CH(R$^2$)—

(wherein $R^2$ is as defined above, and $R^3$ is a hydrogen atom, a $(C_{1-6})$alkyl group, a formyl group, a $(C_{1-3})$-alkylcarbonyl group or a halo$(C_{1-3})$alkylcarbonyl group), X may be the same or different, and is a bromine atom, an iodine atom; a hydroxyl group; a cyano group; a $(C_{1-6})$alkyl group; a halo$(C_{1-10})$alkyl group; a $(C_{2-6})$alkenyl group; a halo$(C_{2-6})$alkenyl group; a $(C_{2-6})$alkynyl group; a $(C_{1-6})$alkoxy group; a halo$(C_{1-6})$ alkoxy group; a $(C_{1-6})$alkylthio group; a halo$(C_{1-6})$ alkylthio group; a $(C_{1-6})$alkylsulfinyl group; a halo$(C_{1-6})$alkylsulfinyl group; a $(C_{1-6})$alkylsulfonyl group; a halo$(C_{1-6})$alkylsulfonyl group; a halo$(C_{1-6})$ alkoxyhalo$(C_{1-6})$alkoxy group; a carboxyl group; a $(C_{1-6})$alkoxycarbonyl group; an unsubstituted aminocarbonyl group; a substituted aminocarbonyl group having one or two substituents which may be the same or different and are selected from the group consisting of $(C_{1-6})$alkyl groups, $(C_{2-6})$alkenyl groups and $(C_{2-6})$ alkynyl groups; a carboxy$(C_{1-6})$alkyl group; a $(C_{1-6})$ alkoxycarbonyl$(C_{1-3})$alkyl group; an unsubstituted aminocarbonyl$(C_{1-3})$alkyl group; a substituted aminocarbonyl$(C_{1-3})$alkyl group having one or two substituents which may be the same or different and are selected from the group consisting of $(C_{1-6})$alkyl groups, $(C_{2-6})$alkenyl groups and $(C_{2-6})$alkynyl groups; a sulfonic acid group; an unsubstituted aminosulfonyl group; a $(C_{1-6})$alkoxysulfonyl group; a substituted aminosulfonyl group having one or two substitutents which may be the same or different and are selected from the group consisting of $(C_{1-6})$alkyl groups, $(C_{2-6})$alkenyl groups and $(C_{2-6})$alkynyl groups; an unsubstituted phenyl group; a substituted phenyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo $(C_{1-6})$alkylthio groups, $(C_{1-6})$alkoxysulfonyl groups and a substituted aminosulfonyl groups having one or two substituents which may be the same or different and are selected from the group consisting of $(C_{1-6})$ alkyl groups, $(C_{2-6})$alkenyl groups and $(C_{2-6})$alkynyl groups; an unsubstituted phenyl$(C_{1-3})$alkyl group; a substituted phenyl$(C_{1-3})$alkyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyloxy group; a substituted phenyloxy group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted pyridyloxy group; or a substituted pyridyloxy group having one or more substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_1-C_6)$alkythio groups and halo$(C_{1-6})$alkylthio groups; and n is an integer of 0 to 4], pest controllers containing the substituted aminoquinazolinone (thione) derivative or salts thereof as the active ingredient, and a method for using the pest controllers.

The present invention also relates to intermediate compounds for producing the above-mentioned derivatives, represented by the general formula (II):

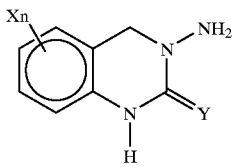

(II)

[wherein, X may be the same or different and is a bromine atom, an iodine atom; a hydroxyl group; a cyano group; a $(C_{1-6})$alkyl group; a halo$(C_{1-10})$alkyl group; a $(C_{2-6})$alkenyl group; a halo$(C_{2-6})$alkenyl group; a $(C_{2-6})$alkynyl group; a $(C_{1-6})$alkoxy group; a halo$(C_{1-6})$alkoxy group; a $(C_{1-6})$ alkylthio group; a halo$(C_{1-6})$alkylthio group; a $(C_{1-6})$ alkylsulfinyl group; a halo$(C_{1-6})$-alkylsulfinyl group; a $(C_{1-6})$alkylsulfonyl group; a halo$(C_{1-6})$alkylsulfonyl groups; a halo$(C_{1-6})$alkoxyhalo$(C_{1-6})$alkoxy group; a carboxyl group; a $(C_{1-6})$alkoxycarbonyl group; an unsubstituted aminocarbonyl group; a substituted aminocarbonyl group having one or two substituents which may be the same or different and are selected from the group consisting of $(C_{1-6})$alkyl groups, $(C_{2-6})$alkenyl groups and $(C_{2-6})$alkynyl groups; a carboxy $(C_{1-6})$alkyl group; a $(C_{1-6})$alkoxycarbonyl$(C_{1-3})$alkyl group; an unsubstituted aminocarbonyl$(C_{1-3})$alkyl group; a substituted aminocarbonyl$(C_{1-3})$alkyl group having one or two substituents which may be the same or different and are selected from the group consisting of $(C_{1-6})$alkyl groups, $(C_{2-6})$alkenyl groups and $(C_{2-6})$alkynyl groups; a sulfonic acid group; a $(C_{1-6})$alkoxysulfonyl group; a sulfonamide group having a hydrogen atom, a $(C_{1-6})$alkyl group, a $(C_{2-6})$alkenyl group or a $(C_{2-6})$alkynyl group on the nitrogen atom; an unsubstituted phenyl group; a substituted phenyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted phenyl$(C_{1-3})$ alkyl group; a substituted phenyl$(C_{1-3})$alkyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo $(C_{1-6})$-alkoxy groups, $(C_{1-6})$alkylthio groups and halo$(C_{1-6})$-alkylthio groups; an unsubstituted phenyloxy group; a substituted phenyloxy group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups and halo$(C_{1-6})$alkylthio groups; an unsubstituted pyridyloxy group; or a substituted pyridyloxy group having one or more substituents which may the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo $(C_{1-6})$alkoxy groups, $(C_{1-6})$alkythio groups and halo$(C_{1-6})$ alkylthio groups; n is an integer of 0 to 4; and Y is an oxygen atom or a sulfur atom].

The pest controllers of the present invention containing, as the active ingredient, substituted aminoquinazolinone (thione) derivatives or salts thereof represented by the general formula (I) possess excellent insecticidal effect at low dosage against greenhouse whitefly (*Trialeurodes vaporariorum*) and the like, which conventional compounds having similar chemical structures do not show insecticidal effects. Thus, the substituted aminoquinazolinone (thione) derivatives of the present invention are excellent pest controllers as compared with conventional ones.

In the definitions of each substituents of the substituted aminoquinazolinone (thione derivatives of the general formula (I) of the present invention, the "halogen atom" means a chlorine atom, a bromine atom, an iodine atom or a fluorine atom. The term "$(C_{1-12})$" means 1 to 12 carbon atoms. The term "$(C_{1-12})$alkyl group" means a linear or branched alkyl group of 1 to 12 carbon atoms, for example an alkyl group such as methyl, ethyl, n-propyl, i-propyl, n-butyl, i-butyl, s-butyl, n-pentyl, n-hexyl, n-heptyl, n-octyl, n-nonyl, n-decyl, n-undecyl, n-dodecyl and the like. The term "halo$(C_{1-10})$alkyl group" means a substituted and linear or branched alkyl group of 1 to 10 carbon atoms having, as the substituent(s), one or more halogen atoms which may be the same or different, for example trifluoromethyl group, pentafluoroethyl group, heptafluoropropyl group and the like. The term "$(C_{2-6})$-alkenyl group" means a linear or branched alkenyl group of 2 to 6 carbon atoms having one or more double bonds. The term "halo$(C_{2-6})$alkenyl group" means a substituted linear or branched alkenyl group of 2 to 6 carbon atoms having, as the substituent(s), one or more halogen atoms which may be the same or different. The term "$(C_{2-6})$alkynyl group" means a linear or branched alkynyl group of 2 to 6 carbon atoms having one or more triple bonds. The term "halo$(C_{2-6})$alkynyl group" means a substituted linear or branched alkynyl group of 2 to 6 carbon atoms having, as the substituent(s), one or more halogen atoms which may be the same or different. The term "5- or 6-membered heterocyclic ring having 1 or more heteroatoms which may be the same or different and are selected from the group consisting of oxygen atom, sulfur atom and nitrogen atom" means any 5- or 6-membered heterocyclic ring for example, furan, thiophene, pyrrole, oxazole, thiazole, pyrazole, imidazole, 1,2,3-thiadiazole, 1,2,4-thiadiazole, 1,2,5-thiadiazole, 1,3,4-thiadiazole, 1,2,4-triazole, pyridine, pyridazine, pyrimidine, pyrazine, pyrrolidine, piperidine, morpholine, thiomorpholine, dithiolane, dithian, piperazine, dioxolan, imidazolidine, tetrahydrofuran and the like.

The substituents of the substituted amino-quinazolinone (thione) derivatives represented by the general formula (I) are preferably as follows: R is a hydrogen atom, a formyl group, a $(C_{1-6})$alkyl group, a $(C_{2-6})$alkenyl group, a $(C_{2-6})$ alkynyl group, a $(C_{1-6})$-alkylcarbonyl group, a $(C_{1-6})$ alkoxycarbonyl group, a $(C_{1-6})$alkylthio group, a halo$(C_{1-6})$ alkylthio group, a phenylcarbonyl group, a substituted phenylcarbonyl group, a substituted phenyl$(C_{1-6})$alkyl group, a substituted phenyl$(C_{2-6})$alkenyl group or a substituted phenyl$(C_{2-6})$alkynyl group; $R^1$ is a pyridyl group, particularly 3-pyridyl group; Y is an oxygen atom or a sulfur atom; Z is a group of the formula,

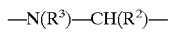

(wherein $R^2$ and $R^3$ are each a hydrogen atom or a $(C_{1-6})$-alkyl group); X is a bromine atom, an iodine atom, a halo$(C_{1-6})$alkyl group, a halo$(C_{1-6})$alkoxy group, a halo$(C_{1-6})$alkylthio group, a halo$(C_{1-6})$alkylsulfinyl group, a halo$(C_{1-6})$alkylsulfonyl group or a phenyl group); and n may be preferably an integer of 0 to 2.

As the salt of the substituted aminoquinazo-linone (thione) derivative of the formula (I), there can be exemplified salts with mineral acids such as hydrochloric acid, sulfuric acid, nitric acid, etc., and salts with alkali metal atoms such as sodium, potassium, etc.

The compound of the formula (II), an intermediate used for producing the substituted amino-quinazolinone (thione)

derivative of the formula (I) can be produced by either of the following processes.

Production Process 1

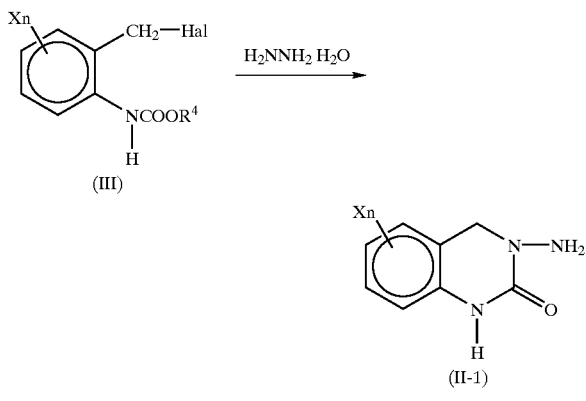

wherein X and n are as defined above, $R^4$ is a $(C_{1-6})$alkyl group, and Hal is a halogen atom.

A compound of the general formula (II-1) can be produced by reacting a compound of the above general formula (III) with hydrazine hydrate in the presence of an inert solvent.

As the inert solvent usable in this reaction, any inert solvent may be used so long as it does not markedly inhibit the progress of the reaction. There can be exemplified alcohols such as methanol, ethanol, propanol, butanol, etc.; halogenated hydrocarbons such as dichloromethane, chloroform, carbon tetrachloride, etc.; aromatic hydrocarbons such as benzene, toluene, xylene, monochlorobenzene etc.; nitrites such as acetonitrile, benzonitrile, etc.; cellosolves such as methyl cellosolve, etc.; ethers such as diethyl ether, diglyme, dioxane, tetrahydrofuran, etc.; amides such as dimethylformamide, dimethylacetamide, 1,3-dimethyl-2-imidazolidinone, 1-methyl-2-pyrrolidone, etc.; dimethyl sulfoxide; sulfolane; and water. These inert solvents may be used singly or as a mixture thereof.

The reaction temperature may be properly chosen in the range of room temperature to the boiling point of the inert solvent used, and ranges preferably from room temperature to 90° C.

Since the reaction is an equimolar reaction, it is sufficient that the compound of the general formula (III) and hydrazine hydrate are used in equimolar amounts, though either of these reactants may be used in excess. It is preferable to use hydrazine hydrate in excess.

Although the reaction time is varied depending on the scale of reaction, the reaction temperature, etc., it ranges from several minutes to 48 hours.

After completion of the reaction, the desired compound is isolated from the reaction mixture containing the desired compound by a conventional method, and if necessary, purified by recrystallization, dry column chromatography, etc., whereby the desired compound can be produced.

The compound of the above general formula (III) can be produced according to Collect. Czech. Chem. Commn. (Vol. 55), 752 (1990).

Production Process 2

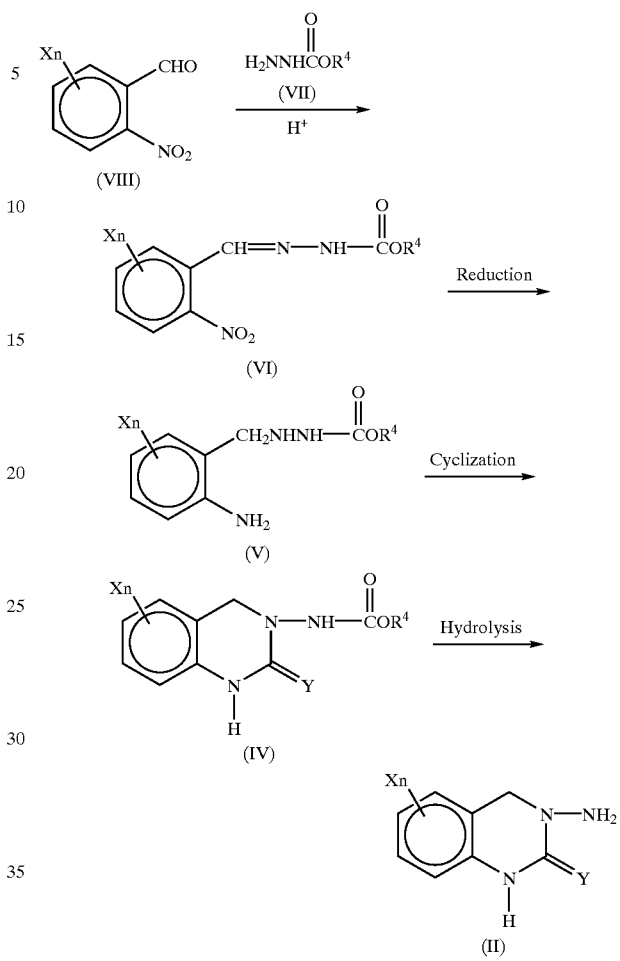

wherein $R^4$, X, Y and n are as defined above.

2-1. General Formula (VIII)→General Formula (VI)

A compound of the general formula (VI) can be produced by reacting a compound of the general formula (VIII) with a compound of the general formula (VII) in the presence of an inert solvent and a catalyst.

As the inert solvent usable in this reaction, there can be used, for example, the inert solvents exemplified in production process 1. These inert solvents may be used singly or as a mixture thereof.

As the catalyst, there can be used inorganic acids (e.g. hydrochloric acid and sulfuric acid), acetic acid, p-toluenesulfonic acid, etc. The amount of the catalyst used may be such that the catalyst is present in the reaction system in an amount of 0.001 wt % to 10 wt % based on the weight of the compound of the general formula (VIII).

Since the reaction is an equimolar reaction, it is sufficient that the compound of the general formula (VIII) and the compound of the general formula (VII) are used in equimolar amounts, though either of these reactants may be used in excess.

The reaction temperature may be properly chosen in the range of room temperature to the boiling point of the inert solvent used, and ranges preferably from room temperature to 90° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

The compound of the general formula (VIII) may be a commercially available one or may be produced by nitrating a substituted benzaldehyde. Further, the compound of the formula (VIII) can be produced according to the method described in Journal of Chemical Society, 1927, pp. 2375–2378.

2-2. General Formula (VI)→General Formula (V)

A compound of the general formula (V) can be produced by reducing the compound of the general formula (VI) with a reducing agent or by catalytic reduction in the presence or absence of an inert solvent.

As the reducing agent, there can be used, for example, metal hydrides such as, $NaBH_3CN$, $LiBH_3CN$, etc. and reducing agents such as $BH_3$, etc. The amount of the reducing agent used may be properly chosen in the range of 1 mole to excess moles (in terms of the number of moles of hydride as reducing agent) per mole of the compound of the general formula (VI).

As the inert solvent usable in the reaction, any inert solvent may be used so long as it does not markedly inhibit the progress of the reaction. There can be exemplified alcohols such as methanol, ethanol, propanol, butanol, etc.; cellosolves such as methyl cellosolve, etc.; ethers such as diethyl ether, diglyme, dioxane, tetrahydrofuran, etc.; esters such as ethyl acetate, etc.; amides such as dimethylformamide, dimethylacetamide, 1,3-dimethyl-2-imidazolidinone, 1-methyl-2-pyrrolidone, etc.; dimethyl sulfoxide; sulfolane; and water. These inert solvents may be used singly or as a mixture thereof.

The reaction is carried out under acidic or neutral conditions in the pH range of 1 to 7, preferably 4 to 6. It is sufficient that the pH is adjusted by adding hydrogen chloride, hydrogen bromide or the like to the reaction system.

The reaction temperature is chosen in the range of 0° C. to the boiling point of the solvent, and ranges preferably from room temperature to 70° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

When catalytic reduction is carried out as the reduction reaction, it is carried out according to, for example, the method described in Shin Jikken Kagaku Koza, Vol. 15–11, Maruzen Co., Ltd. As the inert solvent usable in this case, there can be exemplified alcohols such as methanol, ethanol, propanol, butanol, etc.; cellosolves such as methyl cellosolve, etc.; ethers such as diethyl ether, diglyme, dioxane, tetrahydrofuran, etc.; hydrocarbons such as hexane, cyclohexane, etc.; fatty acids or esters thereof, such as acetic acid, ethyl acetate, etc.; amides such as dimethylformamide, dimethylacetamide, 1,3-dimethyl-2-imidazolidinone, 1-methyl-2-pyrrolidone, etc.; and ureas such as tetramethylurea, etc. These inert solvents may be used singly or as a mixture thereof.

As the catalyst used in the reduction reaction, there can be exemplified typical catalysts for catalytic reduction, such as palladium-carbon, palladium black, platinum dioxide, Raney nickel, etc. The amount of the catalyst used may be properly chosen in the range of 0.1% molar equivalent to 5% molar equivalent, preferably 0.5% molar equivalent to 1% molar equivalent, relative to the compound of the general formula (VI).

The hydrogen pressure in the reaction ranges from atmospheric pressure to 300 atmospheres, preferably from atmospheric pressure to 50 atmospheres.

There action temperature may be properly chosen in the range of room temperature to the boiling point of the inert solvent used, and ranges preferably from room temperature to 70° C.

Although the reaction time is varied depending on the scale of reaction, the reaction temperature, etc., it ranges from several minutes to 48 hours.

After completion of the reaction, the reaction mixture containing the desired compound is treated in the same manner as in the case of using the reducing agent, whereby the desired compound can be produced.

2-3. General Formula (V)→General Formula (IV)

A compound of the general formula (IV) can be produced by reacting the compound of the general formula (V) with 1,1'-carbonylbis-1H-imidazole (CDI), an alkoxycarbonyl halide, phosgene or thiophosgen in the presence of an inert solvent and in the presence or absence of a base.

As the inert solvent usable in the reaction, there can be exemplified ethers such as diethyl ether, diglyme, dioxane, tetrahydrofuran, etc., and aromatic hydrocarbons such as benzene, toluene, xylene, etc. These inert solvents may be used singly or as a mixture thereof.

As the base, an inorganic base or an organic base may be used, and there can be exemplified inorganic bases such as hydroxides and carbonates of alkali metals and alkaline earth metals [e.g. sodium hydroxide, potassium hydroxide, magnesium hydroxide, sodium carbonate, sodium hydrogencarbonate and potassium carbonate], and organic bases such as triethylamine and pyridine. When CDI is used as a reactant, the reaction can be carried out without a base.

The amount of the base used is 2 moles or more per mole of the compound of the general formula (V).

The reaction temperature may be properly chosen in the range of room temperature to the boiling point of the inert solvent used, and ranges preferably from room temperature to 100° C.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

2-4. General Formula (IV)→General Formula (II)

A compound of the general formula (II) can be produced by hydrolyzing the compound of the general formula (IV) under basic condition in the presence of an inert solvent.

As the inert solvent usable in this reaction, there can be exemplified alcohols such as methanol, ethanol, propanol, butanol, etc.; aromatic hydrocarbons such as benzene, toluene, xylene, etc.; ethers such as diethyl ether, diglyme, dioxane, tetrahydrofuran, etc.; and water. These inert solvents may be used singly or as a mixture thereof.

As the base, there can be used hydroxides of alkali metals or alkaline earth metals, such as sodium hydroxide, potassium hydroxide, magnesium hydroxide, etc.

Depending on the alkyl group for $R^4$, the reaction can be carried out also under acidic conditions by using an organic or inorganic acid such as trifluoroacetic acid or hydrochloric acid.

The reaction temperature may be properly chosen in the range of 0° C. to the boiling point of the inert solvent used.

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

Typical examples of the compounds of the general formula (II) produced by production processes 1 and 2 are given in Table 1 but they are not intended in any way to limit the scope of the present invention. In Tables 1, 3 to 4, "Ph" means phenyl group and "Pyr" means pyridyl group.

General Formula (II)

TABLE 1

[Structure: quinazoline-2-thione/one with $X_n$ substituents on benzene ring positions 5,6,7,8; $N_3$-$NH_2$; $N_1$-H; $C_2$=Y] (II)

| No. | Xn | Y | Physical property |
|---|---|---|---|
| II-1 | 5-OH | O | Crystal |
| II-2 | 6-OH | O | Crystal |
| II-3 | 7-OH | O | Crystal |
| II-4 | 8-OH | O | Crystal |
| II-5 | 5-Br | O | |
| II-6 | 6-Br | O | Crystal |
| II-7 | 7-Br | O | |
| II-8 | 8-Br | O | |
| II-9 | 5-I | O | |
| II-10 | 6-I | O | m.p. 202.3–205.0° C. |
| II-11 | 7-I | O | |
| II-12 | 8-I | O | |
| II-13 | 5-$CF_3$ | O | |
| II-14 | 6-$CF_3$ | O | m.p. 155–157.7° C. |
| II-15 | 7-$CF_3$ | O | |
| II-16 | 8-$CF_3$ | O | |
| II-17 | 5-$C_2F_5$ | O | |
| II-18 | 6-$C_2F_5$ | O | m.p. 178.4–183.5° C. |
| II-19 | 7-$C_2F_5$ | O | |
| II-20 | 8-$C_2F_5$ | O | |
| II-21 | 5-i-$C_3F_7$ | O | |
| II-22 | 6-i-$C_3F_7$ | O | m.p. 147.6–149.5° C. |
| II-23 | 7-i-$C_3F_7$ | O | |
| II-24 | 8-i-$C_3F_7$ | O | |
| II-25 | 5-n-$C_6F_{13}$ | O | |
| II-26 | 6-n-$C_6F_{13}$ | O | Crystal |
| II-27 | 7-n-$C_6F_{13}$ | O | |
| II-28 | 8-n-$C_6F_{13}$ | O | |
| II-29 | 5-$OCF_3$ | O | |
| II-30 | 6-$OCF_3$ | O | m.p. 181.5–184.0° C. |
| II-31 | 7-$OCF_3$ | O | |
| II-32 | 8-$OCF_3$ | O | |
| II-33 | 5-$OCH_2$-Ph | O | Crystal |
| II-34 | 6-$OCH_2$-Ph | O | |
| II-35 | 7-$OCH_2$-Ph | O | |
| II-36 | 8-$OCH_2$-Ph | O | Crystal |
| II-37 | 5-$OCHF_2$ | O | |
| II-38 | 6-$OCHF_2$ | O | Crystal |
| II-39 | 7-$OCHF_2$ | O | |
| II-40 | 8-$OCHF_2$ | O | |
| II-41 | 5-$SCF_3$ | O | |
| II-42 | 6-$SCF_3$ | O | |
| II-43 | 7-$SCF_3$ | O | |
| II-44 | 8-$SCF_3$ | O | |
| II-45 | 5-$SC_2F_5$ | O | |
| II-46 | 6-$SC_2F_5$ | O | |
| II-47 | 7-$SC_2F_5$ | O | |
| II-48 | 8-$SC_2F_5$ | O | |
| II-49 | 5-S-i-$C_3F_7$ | O | |
| II-50 | 6-S-i-$C_3F_7$ | O | m.p. 71.2–73.5° C. |
| II-51 | 7-S-i-$C_3F_7$ | O | |
| II-52 | 8-S-i-$C_3F_7$ | O | |
| II-53 | 5-$SOCF_3$ | O | |

TABLE 1-continued

[Structure: quinazoline-2-thione/one with $X_n$ substituents on benzene ring positions 5,6,7,8; $N_3$-$NH_2$; $N_1$-H; $C_2$=Y] (II)

| No. | Xn | Y | Physical property |
|---|---|---|---|
| II-54 | 6-$SOCF_3$ | O | |
| II-55 | 7-$SOCF_3$ | O | |
| II-56 | 8-$SOCF_3$ | O | |
| II-57 | 5-$SO_2CF_3$ | O | |
| II-58 | 6-$SO_2CF_3$ | O | |
| II-59 | 7-$SO_2CF_3$ | O | |
| II-60 | 8-$SO_2CF_3$ | O | |
| II-61 | 5-$SOC_2F_5$ | O | |
| II-62 | 6-$SOC_2F_5$ | O | |
| II-63 | 7-$SOC_2F_5$ | O | |
| II-64 | 8-$SOC_2F_5$ | O | |
| II-65 | 5-$SO_2C_2F_5$ | O | |
| II-66 | 6-$SO_2C_2F_5$ | O | |
| II-67 | 7-$SO_2C_2F_5$ | O | |
| II-68 | 8-$SO_2C_2F_5$ | O | |
| II-69 | 5-SO-i-$C_3F_7$ | O | |
| II-70 | 6-SO-i-$C_3F_7$ | O | |
| II-71 | 7-SO-i-$C_3F_7$ | O | |
| II-72 | 8-SO-i-$C_3F_7$ | O | |
| II-73 | 5-$SO_2$-i-$C_3F_7$ | O | |
| II-74 | 6-$SO_2$-i-$C_3F_7$ | O | |
| II-75 | 7-$SO_2$-i-$C_3F_7$ | O | |
| II-76 | 8-$SO_2$-i-$C_3F_7$ | O | |
| II-77 | 5-$COOC_2H_5$ | O | |
| II-78 | 6-$COOC_2H_5$ | O | |
| II-79 | 7-$COOC_2H_5$ | O | |
| II-80 | 8-$COOC_2H_5$ | O | |
| II-81 | 5-COOH | O | |
| II-82 | 6-COOH | O | |
| II-83 | 7-COOH | O | |
| II-84 | 8-COOH | O | |
| II-85 | 5-Ph | O | |
| II-86 | 6-Ph | O | |
| II-87 | 7-Ph | O | |
| II-88 | 8-Ph | O | |
| II-89 | 5-(p-Cl-Ph) | O | |
| II-90 | 6-(p-Cl-Ph) | O | |
| II-91 | 7-(p-Cl-Ph) | O | |
| II-92 | 8-(p-Cl-Ph) | O | |
| II-93 | 5-O-Ph | O | |
| II-94 | 6-O-Ph | O | |
| II-95 | 7-O-Ph | O | |
| II-96 | 8-O-Ph | O | |
| II-97 | 5-n-$C_4H_9$ | O | |
| II-98 | 6-n-$C_4H_9$ | O | |
| II-99 | 7-n-$C_4H_9$ | O | |
| II-100 | 8-n-$C_4H_9$ | O | |
| II-101 | 5-$OCF_2CHF_2$ | O | |
| II-102 | 6-$OCF_2CHF_2$ | O | m.p. 194.8° C. |
| II-103 | 7-$OCF_2CHF_2$ | O | |
| II-104 | 8-$OCF_2CHF_2$ | O | |
| II-105 | 6-$OCF_2CHFOCF_3$ | O | Crystal |
| II-106 | 6-$OCH(CF_3)_2$ | O | m.p. 238.8–241.0° C. |
| II-107 | 6-O-(m-$CF_3$-Ph) | O | m.p. 204.7–207.9° C. |
| II-108 | 6-O-(3-Cl-5-$CF_3$-2-Pyr) | O | Crystal |

TABLE 2

| No. | $^1$H-NMR [DMSO-$d_6$/TMS, δ (ppm)] |
|---|---|
| II-1 | 4.36(2H,s), 4.65(2H,br), 6.20(1H,d), 6.34(1H,d), 6.89(1H,t), 9.12(1H,br), 9.62(1H,s). |
| II-2 | 4.45(2H,s), 4.65(2H,s), 6.51–6.63(3H,m), 9.00(1H,s), |
| II-3 | 9.60(1H,brs) 4.48(2H,s), 4.65(2H,s), 6.23–6.35(2H,m), |

TABLE 2-continued

| No. | $^1$H-NMR [DMSO-d$_6$/TMS, δ (ppm)] |
|---|---|
| II-4 | 6.85(1H,d), 9.05(1H,s), 9.63(1H,s) |
| | 4.46(2H,s), 4.65(2H,s), 6.57(1H,d), 6.64– |
| II-6 | 6.74(2H,m), 7.95(1H,d), 9.60(1H,brs). |
| | 4.48(2H,s), 4.66(2H,s), 6.74(1H,m), 7.18(1H,m), |
| II-18 | 7.30(1H,m), 9.43(1H,s). |
| | 4.56(2H,s), 4.70(2H,s), 6.95(1H,d), 7.40– |
| II-26 | 7.50(2H,m), 9.83(1H,s). |
| | 4.56(2H,s), 4.70(2H,s), 6.94(1H,d), 7.43– |
| II-33 | 7.48(2H,m), 9.74(1H,s). |
| | 4.48(2H,s), 4.69(2H,s), 5.00(2H,s), 6.30(1H,d), |
| II-36 | 6.45(1H,d), 7.05(1H,t), 7.25–7.40(6H,m). |
| | 4.48(2H,s), 4.68(2H,s), 5.19(2H,s), 6.71(1H,d), |
| | 6.82(1H,t), 6.92(1H,d), 7.30–7.40(3H,m), |
| II-38 | 7.51(2H,d), 8.18(1H,s). |
| | 4.48(2H,s), 4.65(2H,s), 6.76–6.79(1H,d,J = 8.7 Hz), |
| | 6.95–7.00(2H,m), 6.80–7.30(1H,t,J = 7.46), |
| | 9.37(1H,s). |
| II-105 | 4.88(2H,s), 4.64(2H,s), 6.79(1H,d,J = 11.6 Hz), |
| | 7.00(1H,s), 7.06(1H,m), 7.23(1H,t,J = 4 Hz), |
| | 9.43(1H,s). |
| II-108 | 4.46(2H,s), 4.65(2H,s), 6.80(1H,d,J = 11.2 Hz), |
| | 7.01(2H,m), 8.48(1H,s), 8.52(1H,s), 9.38(1H,s). |

Typical examples of process for producing the aminoquinazolinone (thione) derivative of the general formula (I) or salt thereof of the present invention are schematically shown below.

Production Process 3 wherein R, $R^1$, $R^2$, $R^3$, X, n, Y and Hal are as defined above except that each of R and $R^3$ is not a hydrogen atom.

3-1. General Formula (II) →General Formula (I-1)

An aminoquinazolinone (thione) derivative of the general formula (I-1) can be produced by reacting a compound of the general formula (II) with a compound of the general formula (X) in the presence of an inert solvent and a catalyst.

In the case of this reaction, the desired compound can be produced in a manner similar to that described in production process 2-1.

3-2. General Formula (I-1)→General Formula (I-3)

An aminoquinazolinone (thione) derivative of the general formula (I-3) can be produced by reacting the aminoquinazolinone (thione) derivative of the general formula (I-1) with a compound of the general formula (IX) in the presence or absence of an inert solvent and a base.

As the inert solvent usable in this reaction, there can be used, for example, the inert solvents exemplified in production process 1.

As the base, an inorganic base or an organic base may be used. In addition to the inorganic or organic bases exemplified in production process 2-3, there can also be used alkoxides such as $CH_3ONa$, $C_2H_5ONa$, $t-C_4H_9ONa$, $CH_3OK$, $C_2H_5OK$, $t-C_4H_9OK$, etc., and alkali metal hydrides such as NaH, etc. The amount of the base used may be properly chosen in the range of 1 mole to excess moles per mole of the aminoquinazolinone (thione) derivative of the general formula (I-1).

The reaction temperature may be chosen in the range of 0° C. to the boiling point of the inert solvent used, and ranges preferably from room temperature to 70° C.

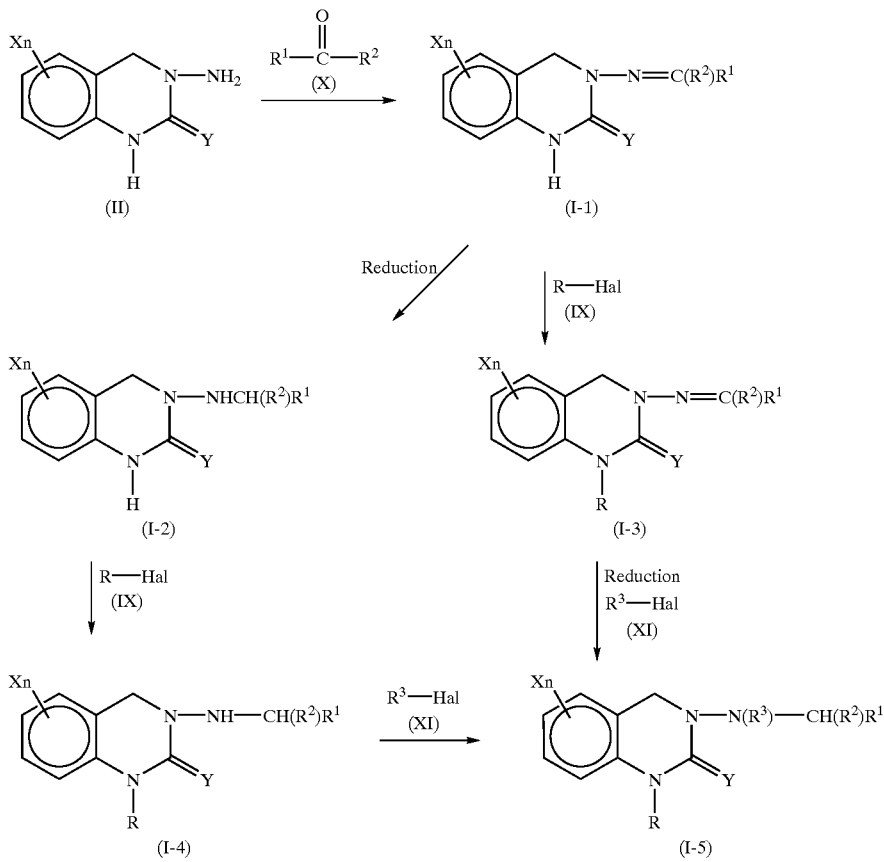

15

Although the reaction time is varied depending on the scale of reaction, the reaction temperature, etc., it ranges from several minutes to 48 hours.

After completion of the reaction, the reaction mixture containing the desired compound is treated in the same manner as in production process 1, whereby the desired compound can be produced.

3-3. General Formula (I-1)→General Formula (I-2)

In the case of this reaction, the desired compound can be produced in a manner similar to that described in production process 2-2.

3-4. General Formula (I-2)→General Formula (I-4)

An aminoquinazolinone (thione) derivative of the general formula (I-4) can be produced by reacting the aminoquinazolinone (thione) derivative of the general formula (I-2) with the compound of the formula (IX) in the presence or absence of an inert solvent and a base.

In the case of this reaction, the desired compound can be produced in a manner similar to that described in production process 3-2.

3-5. General Formula (I-4)→General Formula (I-5)

An aminoquinazolinone (thione) derivative of the general formula (I-5) can be produced by reacting the aminoquinazolinone (thione) derivative of the general formula (I-4) with a compound of the general formula (XI) in the presence or absence of an inert solvent and a base.

In case of this reaction, the desired compound can be produced in a manner similar to that described in production process 3-2.

3-6. General Formula (I-3)→General Formula (I-5)

In case of this reaction, the desired compound can be produced in a manner similar to that described in production process 2-2.

Typical examples of the aminoquinazolinone (thione) derivative of the formula (I) or salt thereof of the present invention are given in Tables 3 and 4 but they are not intended in any way to limit the scope of the present invention.

The abbreviations in Table 3 and Table 4 stand for the following substituents:

c: alicyclic hydrocarbon group

Ph: phenyl group, $Q_1$: 2-pyridyl group, $Q_2$: 3-pyridyl group, $Q_3$: 4-pyridyl group, $Q_4$: 2-pyridyl-N-oxide group, $Q_5$: 3-pyridyl-N-oxide group, $Q_6$: 4-pyridyl-N-oxide group, $Q_7$: thiazol-5-yl group, $Q_8$: furan-2-yl group, $Q_9$: 1,3-dioxolan-2-yl group, $Q_{10}$: phthalimid-1-yl group, $Q_{11}$: thiophene-2-yl group, $Q_{12}$: 5-chloro-1,3-dimethylpyrazole-4-yl group.

TABLE 3

($R^1$ = $Q_2$, $R^2$ = H, Y = O, except for the group noted specially.)

| No. | R | Xn | Physical property |
| --- | --- | --- | --- |
| 1 | H | 5-OH | m.p. 293–295° C. |
| 2 | H | 6-OH | |
| 3 | H | 7-OH | |
| 4 | H | 8-OH | m.p. >300° C. |
| 5 | H | 5-Br | |
| 6 | H | 6-Br | m.p. >300° C. |
| 7 | H | 7-Br | |
| 8 | H | 8-Br | |
| 9 | H | 5-I | |
| 10 | H | 6-I | m.p. >300° C. |
| 11 | H | 7-I | |
| 12 | H | 8-I | |
| 13 | H | 5-$CF_3$ | |
| 14 | H | 6-$CF_3$ | m.p. 227.6–286.7° C. |
| 15 | H | 7-$CF_3$ | |
| 16 | H | 8-$CF_3$ | |
| 17 | H | 5-$C_2F_5$ | |
| 18 | H | 6-$C_2F_5$ | m.p. 298–300° C. |
| 19 | H | 7-$C_2F_5$ | |
| 20 | H | 8-$C_2F_5$ | |
| 21 | H | 5-i-$C_3F_7$ | |
| 22 | H | 6-i-$C_3F_7$ | m.p. >300° C. |
| 23 | H | 7-i-$C_3F_7$ | |
| 24 | H | 8-i-$C_3F_7$ | |
| 25 | H | 5-n-$C_6F_{13}$ | |
| 26 | H | 6-n-$C_6F_{13}$ | m.p. >300° C. |
| 27 | H | 7-n-$C_6F_{13}$ | |
| 28 | H | 8-n-$C_6F_{13}$ | |
| 29 | H | 5-$OCF_3$ | |
| 30 | H | 6-$OCF_3$ | m.p. 264.0–266.0° C. |
| 31 | H | 7-$OCF_3$ | |
| 32 | H | 8-$OCF_3$ | |
| 33 | H | 5-$CH_2$-Ph | |
| 34 | H | 6-$CH_2$-Ph | |
| 35 | H | 7-$CH_2$-Ph | |
| 36 | H | 8-$CH_2$-Ph | |
| 37 | H | 5-$OCHF_2$ | |
| 38 | H | 6-$OCHF_2$ | m.p. 260.1–264.5° C. |
| 39 | H | 7-$OCHF_2$ | |
| 40 | H | 8-$OCHF_2$ | |
| 41 | H | 5-$SCF_3$ | |
| 42 | H | 6-$SCF_3$ | |
| 43 | H | 7-$SCF_3$ | |
| 44 | H | 8-$SCF_3$ | |
| 45 | H | 5-$SC_2F_5$ | |
| 46 | H | 6-$SC_2F_5$ | |
| 47 | H | 7-$SC_2F_5$ | |
| 48 | H | 8-$SC_2F_5$ | |
| 49 | H | 5-S-i-$C_3F_7$ | |
| 50 | H | 6-S-i-$C_3F_7$ | m.p. 252.4–255.0° C. |
| 51 | H | 7-S-i-$C_3F_7$ | |
| 52 | H | 8-S-i-$C_3F_7$ | |
| 53 | H | 5-$SOCF_3$ | |
| 54 | H | 6-$SOCF_3$ | |
| 55 | H | 7-$SOCF_3$ | |
| 56 | H | 8-$SOCF_3$ | |
| 57 | H | 5-$SO_2CF_3$ | |
| 58 | H | 6-$SO_2CF_3$ | |
| 59 | H | 7-$SO_2CF_3$ | |
| 60 | H | 8-$SO_2CF_3$ | |
| 61 | H | 5-$SOC_2F_5$ | |
| 62 | H | 6-$SOC_2F_5$ | |
| 63 | H | 7-$SOC_2F_5$ | |
| 64 | H | 8-$SOC_2F_5$ | |
| 65 | H | 5-$SO_2C_2F_5$ | |
| 66 | H | 6-$SO_2C_2F_5$ | |
| 67 | H | 7-$SO_2C_2F_5$ | |
| 68 | H | 8-$SO_2C_2F_5$ | |
| 69 | H | 5-SO-i-$C_3F_7$ | |
| 70 | H | 6-SO-i-$C_3F_7$ | |
| 71 | H | 7-SO-i-$C_3F_7$ | |
| 72 | H | 8-SO-i-$C_3F_7$ | |
| 73 | H | 5-$SO_2$-i-$C_3F_7$ | |
| 74 | H | 6-$SO_2$-i-$C_3F_7$ | |

TABLE 3-continued ($R^1 = Q_2$, $R^2 = H$, $Y = O$, except for the group noted specially.)

| No. | R | Xn | Physical property |
|---|---|---|---|
| 75 | H | 7-$SO_2$-i-$C_3F_7$ | |
| 76 | H | 8-$SO_2$-i-$C_3F_7$ | |
| 77 | H | 5-$COOC_2H_5$ | |
| 78 | H | 6-$COOC_2H_5$ | m.p. 274–278° C. |
| 79 | H | 7-$COOC_2H_5$ | |
| 80 | H | 8-$COOC_2H_5$ | |
| 81 | H | 5-COOH | |
| 82 | H | 6-COOH | |
| 83 | H | 7-COOH | |
| 84 | H | 8-COOH | |
| 85 | H | 5-Ph | |
| 86 | H | 6-Ph | m.p. 250.9–253.8° C. |
| 87 | H | 7-Ph | |
| 88 | H | 8-Ph | |
| 89 | H | 5-(4-Cl-Ph) | |
| 90 | H | 6-(4-Cl-Ph) | m.p. 276–278° C. |
| 91 | H | 7-(4-Cl-Ph) | |
| 92 | H | 8-(4-Cl-Ph) | |
| 93 | H | 5-O-Ph | |
| 94 | H | 6-O-Ph | |
| 95 | H | 7-O-Ph | |
| 96 | H | 8-O-Ph | |
| 97 | H | 5-n-$C_4H_9$ | |
| 98 | H | 6-n-$C_4H_9$ | |
| 99 | H | 7-n-$C_4H_9$ | |
| 100 | H | 8-n-$C_4H_9$ | |
| 101 | $CH_3$ | 5-I | |
| 102 | $CH_3$ | 6-I | m.p. 181.4–185.3° C. |
| 103 | $CH_3$ | 7-I | |
| 104 | $CH_3$ | 8-I | |
| 105 | $C_2H_5$ | 5-I | |
| 106 | $C_2H_5$ | 6-I | m.p. 191.5–194.5° C. |
| 107 | $C_2H_5$ | 7-I | |
| 108 | $C_2H_5$ | 8-I | |
| 109 | n-$C_5H_{11}$ | 5-I | |
| 110 | n-$C_5H_{11}$ | 6-I | nD 1.4126 (28.5° C.) |
| 111 | n-$C_5H_{11}$ | 7-I | |
| 112 | n-$C_5H_{11}$ | 8-I | |
| 113 | $CH_2C\equiv CH$ | 5-I | |
| 114 | $CH_2C\equiv CH$ | 6-I | m.p. 214–217° C. |
| 115 | $CH_2C\equiv CH$ | 7-I | |
| 116 | $CH_2C\equiv CH$ | 8-I | |
| 117 | $CH_2CH=CH_2$ | 5-I | |
| 118 | $CH_2CH=CH_2$ | 6-I | m.p. 162–164° C. |
| 119 | $CH_2CH=CH_2$ | 7-I | |
| 120 | $CH_2CH=CH_2$ | 8-I | |
| 121 | $CH_2OC_2H_5$ | 5-I | |
| 122 | $CH_2OC_2H_5$ | 6-I | m.p. 111.3–161.7° C. |
| 123 | $CH_2OC_2H_5$ | 7-I | |
| 124 | $CH_2OC_2H_5$ | 8-I | |
| 125 | $CH_2$(4-Cl-Ph) | 5-I | |
| 126 | $CH_2$(4-Cl-Ph) | 6-I | m.p. 146–149° C. |
| 127 | $CH_2$(4-Cl-Ph) | 7-I | |
| 128 | $CH_2$(4-Cl-Ph) | 8-I | |
| 129 | $COCH_3$ | 5-I | |
| 130 | $COCH_3$ | 6-I | m.p. 186–188° C. |
| 131 | $COCH_3$ | 7-I | |
| 132 | $COCH_3$ | 8-I | |
| 133 | $COC_2H_5$ | 5-I | |
| 134 | $COC_2H_5$ | 6-I | m.p. 135–139° C. |
| 135 | $COC_2H_5$ | 7-I | |
| 136 | $COC_2H_5$ | 8-I | |
| 137 | $SO_2CH_3$ | 5-I | |
| 138 | $SO_2CH_3$ | 6-I | m.p. 174–181° C. |
| 139 | $SO_2CH_3$ | 7-I | |
| 140 | $SO_2CH_3$ | 8-I | |
| 141 | $SO_2Ph$ | 5-I | |
| 142 | $SO_2Ph$ | 6-I | m.p. 199–205° C. |
| 143 | $SO_2Ph$ | 7-I | |
| 144 | $SO_2Ph$ | 8-I | |
| 145 | H | 5-$OCF_2CHF_2$ | |
| 146 | H | 6-$OCF_2CHF_2$ | m.p. 251.6–263.3° C. |
| 147 | H | 7-$OCF_2CHF_2$ | |
| 148 | H | 8-$OCF_2CHF_2$ | |
| 149 | CO-c-$C_3H_5$ | 5-I | |
| 150 | CO-c-$C_3H_5$ | 6-I | m.p. 172–175° C. |
| 151 | CO-c-$C_3H_5$ | 7-I | |
| 152 | CO-c-$C_3H_5$ | 8-I | |
| 153 | H | 5-(4-$CH_3$O-Ph) | |
| 154 | H | 6-(4-$CH_3$O-Ph) | m.p. 242° C. |
| 155 | H | 7-(4-$CH_3$O-Ph) | |
| 156 | H | 8-(4-$CH_3$O-Ph) | |
| 157 | H | 5-(3-$CH_3$O-Ph | |
| 158 | H | 6-(3-$CH_3$O-Ph) | m.p. 192–199° C. |
| 159 | H | 7-(3-$CH_3$O-Ph) | |
| 160 | H | 8-(3-$CH_3$O-Ph) | |
| 161 | H | 5-(3-$NO_2$-Ph) | |
| 162 | H | 6-(3-$NO_2$-Ph) | m.p. >300° C. |
| 163 | H | 7-(3-$NO_2$-Ph) | |
| 164 | H | 8-(3-$NO_2$-Ph) | |
| 165 | H | 5-COOH | |
| 166 | H | 6-COOH | m.p. >300° C. |
| 167 | H | 7-COOH | |
| 168 | H | 8-COOH | |
| 169 | H | 5-$COOCH_3$ | |
| 170 | H | 6-$COOCH_3$ | m.p. 270.5–279.6° C. |
| 171 | H | 7-$COOCH_3$ | |
| 172 | H | 8-$COOCH_3$ | |
| 173 | H | 5-$CON(C_2H_5)_2$ | |
| 174 | H | 6-$CON(C_2H_5)_2$ | m.p. 254.9–278.1° C. |
| 175 | H | 7-$CON(C_2H_5)_2$ | |
| 176 | H | 8-$CON(C_2H_5)_2$ | |
| 177 | H | 6-Cl-7-$CF_2H$ | m.p. 295° C. |
| 178 | H | 6-$C_3F_{7-i}$ | m.p. 227.1–227.3° C. ($Q_2$: N-methylpyridium iodide salt) |
| 178.1 | H | 6-$OCF_2CHFOCF_3$ | m.p. 240.2–241.3° C. |
| 178.2 | H | 6-O-(3-Cl-5-$CF_3$-2-Pyr) | m.p. 284.7–288.5° C. |
| 178.3 | H | 6-O-(3-$CF_3$-Ph) | m.p. 239.1–240.9° C. |
| 178.4 | H | 6-O-CH($CF_3$)$_2$ | m.p. >300° C. |
| 178.5 | H | 6-F | m.p. 232.2–236.3° C. $R^1 = Q_{12}$ |
| 178.6 | $COOCH_3$ | 6-$C_3F_{7-i}$ | m.p. 160–165° C. |

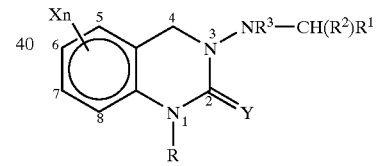

TABLE 4

($R^2 = H$, $Y = O$ and $R^3 = H$, except for the group noted specially.)

| No | R | $R^1$ | Xn | Physical property |
|---|---|---|---|---|
| 179 | H | $Q_2$ | 5-OH | |
| 180 | H | $Q_2$ | 6-OH | m.p. 223–225° C. |
| 181 | H | $Q_2$ | 7-OH | m.p. 258–259° C. |
| 182 | H | $Q_2$ | 8-OH | m.p. 177–180° C. |
| 183 | H | $Q_2$ | 5-Br | |
| 184 | H | $Q_2$ | 6-Br | m.p. >300° C. |
| 185 | H | $Q_2$ | 7-Br | |
| 186 | H | $Q_2$ | 8-Br | |
| 187 | H | $Q_2$ | 5-I | |
| 188 | H | $Q_2$ | 6-I | |
| 189 | H | $Q_2$ | 7-I | |
| 190 | H | $Q_2$ | 8-I | |
| 191 | H | $Q_2$ | 5-$CF_3$ | |
| 192 | H | $Q_2$ | 6-$CF_3$ | m.p. 191.0–193.1° C. |
| 193 | H | $Q_2$ | 7-$CF_3$ | |
| 194 | H | $Q_2$ | 8-$CF_3$ | |
| 195 | H | $Q_2$ | 5-$C_2F_5$ | |
| 196 | H | $Q_2$ | 6-$C_2F_5$ | |

TABLE 4-continued ($R^2$ = H, Y = O and $R^3$ = H, except for the group noted specially.)

| No | R | $R^1$ | Xn | Physical property |
|---|---|---|---|---|
| 197 | H | $Q_2$ | 7-$C_2F_5$ | |
| 198 | H | $Q_2$ | 8-$C_2F_5$ | |
| 199 | H | $Q_2$ | 5-i-$C_3F_7$ | |
| 200 | H | $Q_2$ | 6-i-$C_3F_7$ | m.p. 159.4–161.0° C. |
| 201 | H | $Q_2$ | 7-i-$C_3F_7$ | |
| 202 | H | $Q_2$ | 8-i-$C_3F_7$ | |
| 203 | H | $Q_2$ | 5-n-$C_6F_{13}$ | |
| 204 | H | $Q_2$ | 6-n-$C_6F_{13}$ | m.p. 153.9–164.7° C. |
| 205 | H | $Q_2$ | 7-n-$C_6F_{13}$ | |
| 206 | H | $Q_2$ | 8-n-$C_6F_{13}$ | |
| 207 | H | $Q_2$ | 5-$OCF_3$ | |
| 208 | H | $Q_2$ | 6-$OCF_3$ | nD 1.5233 (22.6° C.) |
| 209 | H | $Q_2$ | 7-$QCF_3$ | |
| 210 | H | $Q_2$ | 8-$QCF_3$ | |
| 211 | H | $Q_2$ | 5-$CH_2$-Ph | |
| 212 | H | $Q_2$ | 6-$CH_2$-Ph | |
| 213 | H | $Q_2$ | 7-$CH_2$-Ph | |
| 214 | H | $Q_2$ | 8-$CH_2$-Ph | |
| 215 | H | $Q_2$ | 5-$OCHF_2$ | |
| 216 | H | $Q_2$ | 6-$OCHF_2$ | m.p. 129.7–130.2° C. |
| 217 | H | $Q_2$ | 7-$QCHF_2$ | |
| 218 | H | $Q_2$ | 8-$QCHF_2$ | |
| 219 | H | $Q_2$ | 5-$SCF_3$ | |
| 220 | H | $Q_2$ | 6-$SCF_3$ | |
| 221 | H | $Q_2$ | 7-$SCF_3$ | |
| 222 | H | $Q_2$ | 8-$SCF_3$ | |
| 223 | H | $Q_2$ | 5-$SC_2F_5$ | |
| 224 | H | $Q_2$ | 6-$SC_2F_5$ | |
| 225 | H | $Q_2$ | 7-$SC_2F_5$ | |
| 226 | H | $Q_2$ | 8-$SC_2F_5$ | |
| 227 | H | $Q_2$ | 5-S-i-$C_3F_7$ | |
| 228 | H | $Q_2$ | 6-S-i-$C_3F_7$ | m.p. 50.3–53.1° C. |
| 229 | H | $Q_2$ | 7-S-i-$C_3F_7$ | |
| 230 | H | $Q_2$ | 8-S-i-$C_3F_7$ | |
| 231 | H | $Q_2$ | 5-$SOCF_3$ | |
| 232 | H | $Q_2$ | 6-$SOCF_3$ | |
| 233 | H | $Q_2$ | 7-$SOCF_3$ | |
| 234 | H | $Q_2$ | 8-$SOCF_3$ | |
| 235 | H | $Q_2$ | 5-$SO_2CF_3$ | |
| 236 | H | $Q_2$ | 6-$SO_2CF_3$ | |
| 237 | H | $Q_2$ | 7-$SO_2CF_3$ | |
| 238 | H | $Q_2$ | 8-$SO_2CF_3$ | |
| 239 | H | $Q_2$ | 5-$SOC_2F_5$ | |
| 240 | H | $Q_2$ | 6-$SOC_2F_5$ | |
| 241 | H | $Q_2$ | 7-$SOC_2F_5$ | |
| 242 | H | $Q_2$ | 8-$SOC_2F_5$ | |
| 243 | H | $Q_2$ | 5-$SO_2C_2F_5$ | |
| 244 | H | $Q_2$ | 6-$SO_2C_2F_5$ | |
| 245 | H | $Q_2$ | 7-$SO_2C_2F_5$ | |
| 246 | H | $Q_2$ | 8-$SO_2C_2F_5$ | |
| 247 | H | $Q_2$ | 5-SO-i-$C_3F_7$ | |
| 248 | H | $Q_2$ | 6-SO-i-$C_3F_7$ | |
| 249 | H | $Q_2$ | 7-SO-i-$C_3F_7$ | |
| 250 | H | $Q_2$ | 8-SO-i-$C_3F_7$ | |
| 251 | H | $Q_2$ | 5-$SO_2$-i-$C_3F_7$ | |
| 252 | H | $Q_2$ | 6-$SO_2$-i-$C_3F_7$ | |
| 253 | H | $Q_2$ | 7-$SO_2$-i-$C_3F_7$ | |
| 254 | H | $Q_2$ | 8-$SO_2$-i-$C_3F_7$ | |
| 255 | H | $Q_2$ | 5-$COOC_2H_5$ | |
| 256 | H | $Q_2$ | 6-$COOC_2H_5$ | |
| 257 | H | $Q_2$ | 7-$COOC_2H_5$ | |
| 258 | H | $Q_2$ | 8-$COOC_2H_5$ | |
| 259 | H | $Q_2$ | 5-COOH | |
| 260 | H | $Q_2$ | 6-COOH | |
| 261 | H | $Q_2$ | 7-COOH | |
| 262 | H | $Q_2$ | 8-COOH | |
| 263 | H | $Q_2$ | 5-Ph | |
| 264 | H | $Q_2$ | 6-Ph | |
| 265 | H | $Q_2$ | 7-Ph | |
| 266 | H | $Q_2$ | 8-Ph | |
| 267 | H | $Q_2$ | 5-(4-Cl-Ph) | |
| 268 | H | $Q_2$ | 6-(4-Cl-Ph) | |
| 269 | H | $Q_2$ | 7-(4-Cl-Ph) | |
| 270 | H | $Q_2$ | 8-(4-Cl-Ph) | |
| 271 | H | $Q_2$ | 5-O-Ph | |
| 272 | H | $Q_2$ | 6-O-Ph | |
| 273 | H | $Q_2$ | 7-O-Ph | |
| 274 | H | $Q_2$ | 8-O-Ph | |
| 275 | H | $Q_2$ | 5-n-$C_4H_9$ | |
| 276 | H | $Q_2$ | 6-n-$C_4H_9$ | |
| 277 | H | $Q_2$ | 7-n-$C_4H_9$ | |
| 278 | H | $Q_2$ | 8-n-$C_4H_9$ | |
| 279 | H | $Q_2$ | 5-$OCF_2CHF_2$ | |
| 280 | H | $Q_2$ | 6-$OCF_2CHF_2$ | m.p. 168.7–173.9° C. |
| 281 | H | $Q_2$ | 7-$OCF_2CHF_2$ | |
| 282 | H | $Q_2$ | 8-$OCF_2CHF_2$ | |
| 283 | H | Qs | 5-$CF(CF_3)_2$ | |
| 284 | H | Qs | 6-$CF(CF_3)_2$ | m.p. 239.7–243.5° C. |
| 285 | H | Qs | 7-$CF(CF_3)_2$ | |
| 286 | H | Qs | 8-$CF(CF_3)_2$ | |
| 287 | H | $Q_2$ | 6-$CF(CF_3)_2$ | m.p. 209.9–213.4° C. ($R^3$=$COCF_3$) |
| 288 | $CH_3$ | $Q_2$ | 5-$OCF_3$ | |
| 289 | $CH_3$ | $Q_2$ | 6-$OCF_3$ | nD 1.5467 (23.6° C.) |
| 290 | $CH_3$ | $Q_2$ | 7-$OCF_3$ | |
| 291 | $CH_3$ | $Q_2$ | 8-$OCF_3$ | |
| 292 | $C_2H_5$ | $Q_2$ | 5-$OCF_3$ | |
| 293 | $C_2H_5$ | $Q_2$ | 6-$OCF_3$ | nD 1.5360 (24.3° C.) |
| 294 | $C_2H_5$ | $Q_2$ | 7-$OCF_3$ | |
| 295 | $C_2H_5$ | $Q_2$ | 8-$OCF_3$ | |
| 296 | $COCH_3$ | $Q_2$ | 5-$OCF_3$ | |
| 297 | $COCH_3$ | $Q_2$ | 6-$OCF_3$ | nD 1.5478 (24.1° C.) |
| 298 | $COCH_3$ | $Q_2$ | 7-$OCF_3$ | |
| 299 | $COCH_3$ | $Q_2$ | 8-$OCF_3$ | |
| 300 | $CQC_2H_5$ | $Q_2$ | 5-$OCF_3$ | |
| 301 | $COC_2H_5$ | $Q_2$ | 6-$OCF_3$ | nD 1.5174 (25.9° C.) |
| 302 | $COC_2H_5$ | $Q_2$ | 7-$OCF_3$ | |
| 303 | $CQC_2H_5$ | $Q_2$ | 8-$OCF_3$ | |
| 304 | $CH_2CH=CH_2$ | $Q_2$ | 5-$OCF_3$ | |
| 305 | $CH_2CH=CH_2$ | $Q_2$ | 6-$OCF_3$ | m.p. 92.5° C. |
| 306 | $CH_2CH=CH_2$ | $Q_2$ | 7-$OCF_3$ | |
| 307 | $CH_2CH=CH_2$ | $Q_2$ | 8-$OCF_3$ | |
| 308 | $CH_2C\equiv CH$ | $Q_2$ | 5-$OCF_3$ | |
| 309 | $CH_2C\equiv CH$ | $Q_2$ | 6-$OCF_3$ | nD 1.5325 (24.2° C.) |
| 310 | $CH_2C\equiv CH$ | $Q_2$ | 7-$OCF_3$ | |
| 311 | $CH_2C\equiv CH$ | $Q_2$ | 8-$QCF_3$ | |
| 312 | $CH(CH_3)_2$ | $Q_2$ | 5-$OCF_3$ | |
| 313 | $CH(CH_3)_2$ | $Q_2$ | 6-$OCF_3$ | nD 1.5370 (24.8° C.) |
| 324 | $CH(CH_3)_2$ | $Q_2$ | 7-$QCF_3$ | |
| 315 | $CH(CH_3)_2$ | $Q_2$ | 8-$QCF_3$ | |
| 316 | H | $Q_2$ | 6-$QCF_3$ | nD 1.5380 (26.0° C.) ($R^3$=$COC_2H_5$) |
| 317 | $CH_2C\equiv CH$ | $Q_2$ | 5-Br | |
| 318 | $CH_2C\equiv CH$ | $Q_2$ | 6-Br | nD 1.5760 (26.2° C.) |
| 319 | $CH_2C\equiv CH$ | $Q_2$ | 7-Br | |
| 320 | $CH_2C\equiv CH$ | $Q_2$ | 8-Br | |
| 321 | $CH_2SCH_3$ | $Q_2$ | 5-Br | |
| 322 | $CH_2SCH_3$ | $Q_2$ | 6-Br | nD 1.6030 (27.0° C.) |
| 323 | $CH_2SCH_3$ | $Q_2$ | 7-Br | |
| 324 | $CH_2SCH_3$ | $Q_2$ | 8-Br | |
| 325 | $C_2H_5$ | $Q_2$ | 5-Br | |
| 326 | $C_2H_5$ | $Q_2$ | 6-Br | nD 1.5974 (26.9° C.) |
| 327 | $C_2H_5$ | $Q_2$ | 7-Br | |
| 328 | $C_2H_5$ | $Q_2$ | 8-Br | |
| 329 | i-$C_3H_7$ | $Q_2$ | 5-Br | |
| 330 | i-$C_3H_7$ | $Q_2$ | 6-Br | nD 1.4680 (28.0° C.) |
| 331 | i-$C_3H_7$ | $Q_2$ | 7-Br | |
| 332 | i-$C_3H_7$ | $Q_2$ | 8-Br | |
| 333 | $COCH_3$ | $Q_2$ | 5-Br | |
| 334 | $COCH_3$ | $Q_2$ | 6-Br | nD 1.5930 (27.2° C.) |
| 335 | $COCH_3$ | $Q_2$ | 7-Br | |
| 336 | $COCH_3$ | $Q_2$ | 8-Br | |
| 337 | $COC_2H_5$ | $Q_2$ | 5-Br | |
| 338 | $COC_2H_5$ | $Q_2$ | 6-Br | nD 1.5861 (26.8° C.) |
| 339 | $COC_2H_5$ | $Q_2$ | 7-Br | |
| 340 | $COC_2H_5$ | $Q_2$ | 8-Br | |
| 341 | $CH_2$-(4-Cl-Ph) | $Q_2$ | 5-Br | |
| 342 | $CH_2$-(4-Cl-Ph) | $Q_2$ | 6-Br | nD 1.5885 (27.3° C.) |
| 343 | $CH_2$-(4-Cl-Ph) | $Q_2$ | 7-Br | |
| 344 | $CH_2$-(4-Cl-Ph) | $Q_2$ | 8-Br | |

TABLE 4-continued ($R^2$ = H, Y = O and $R^3$ = H, except for the group noted specially.)

| No | R | $R^1$ | Xn | Physical property |
|---|---|---|---|---|
| 345 | CO-Ph | $Q_2$ | 5-Br | |
| 346 | CO-Ph | $Q_2$ | 6-Br | m.p. > 300° C. |
| 347 | CO-Ph | $Q_2$ | 7-Br | |
| 348 | CO-Ph | $Q_2$ | 8-Br | |
| 349 | $CH_3$ | $Q_2$ | 5-$OCHF_2$ | |
| 350 | $CH_3$ | $Q_2$ | 6-$OCHF_2$ | nD 1.5613 (27.9° C.) |
| 351 | $CH_3$ | $Q_2$ | 7-$OCHF_2$ | |
| 352 | $CH_3$ | $Q_2$ | 8-$OCHF_2$ | |
| 353 | $C_2H_5$ | $Q_2$ | 5-$OCHF_2$ | |
| 354 | $C_2H_5$ | $Q_2$ | 6-$OCHF_2$ | nD 1.5354 (26.4° C.) |
| 355 | $C_2H_5$ | $Q_2$ | 7-$OCHF_2$ | |
| 356 | $C_2H_5$ | $Q_2$ | 8-$OCHF_2$ | |
| 357 | n-$C_8H_{17}$ | $Q_2$ | 5-$OCHF_2$ | |
| 358 | n-$C_8H_{17}$ | $Q_2$ | 6-$OCHF_2$ | nD 1.5590 (25.8° C.) |
| 359 | n-$C_8H_{17}$ | $Q_2$ | 7-$OCHF_2$ | |
| 360 | n-$C_8H_{17}$ | $Q_2$ | 8-OCHF | |
| 361 | $CH_2$-(2-$NO_2$-Ph) | $Q_2$ | 5-$OCHF_2$ | |
| 362 | $CH_2$-(2-$NO_2$-Ph) | $Q_2$ | 6-$OCHF_2$ | nD 1.5917 (27.90C) |
| 363 | $CH_2$-(2-$NO_2$-Ph) | $Q_2$ | 7-$OCHF_2$ | |
| 364 | $CH_2$-(2-$NO_2$-Ph) | $Q_2$ | 8-$OCHF_2$ | |
| 365 | i-$C_4H_9$ | $Q_2$ | 5-$OCHF_2$ | |
| 366 | i-$C_4H_9$ | $Q_2$ | 6-$OCHF_2$ | nD 1.5557 (26.4° C.) |
| 367 | i-$C_4H_9$ | $Q_2$ | 7-$OCHF_2$ | |
| 368 | i-$C_4H_9$ | $Q_2$ | 8-$OCHF_2$ | |
| 369 | $CH_2$-(4-$CH_3$O-Ph) | $Q_2$ | 5-$OCHF_2$ | |
| 370 | $CH_2$-(4-$CH_3$O-Ph) | $Q_2$ | 6-$OCHF_2$ | nD 1.5668 (26.5° C.) |
| 371 | $CH_2$-(4-$CH_3$O-Ph) | $Q_2$ | 7-$OCHF_2$ | |
| 372 | $CH_2$-(4-$CH_3$O-Ph) | $Q_2$ | 8-$OCHF_2$ | |
| 373 | $COCH_3$ | $Q_2$ | 5-$OCHF_2$ | |
| 374 | $COCH_3$ | $Q_2$ | 6-$OCHF_2$ | nD 1.5503 (26.1° C.) |
| 375 | $COCH_3$ | $Q_2$ | 7-$OCHF_2$ | |
| 376 | $COCH_3$ | $Q_2$ | 8-$OCHF_2$ | |
| 377 | $COC_2H_5$ | $Q_2$ | 5-$OCHF_2$ | |
| 378 | $COC_2H_5$ | $Q_2$ | 6-$OCHF_2$ | nD 1.5470 (26.2° C.) |
| 379 | $COC_2H_5$ | $Q_2$ | 7-$OCHF_2$ | |
| 380 | $COC_2H_5$ | $Q_2$ | 8-$OCHF_2$ | |
| 381 | CO-i-$C_3H_7$ | $Q_2$ | 5-$OCHF_2$ | |
| 382 | CO-i-$C_3H_7$ | $Q_2$ | 6-$OCHF_2$ | nD 1.5196 (28.3° C.) |
| 383 | CO-i-$C_3H_7$ | $Q_2$ | 7-$OCHF_2$ | |
| 384 | CO-i-$C_3H_7$ | $Q_2$ | 8-$OCHF_2$ | |
| 385 | CO-$O_{11}$ | $Q_2$ | 5-$OCHF_2$ | |
| 386 | CO-$O_{11}$ | $Q_2$ | 6-$OCHF_2$ | m.p. 148–155° C. |
| 387 | CO-$O_{11}$ | $Q_2$ | 7-$OCHF_2$ | |
| 388 | CO-$O_{11}$ | $Q_2$ | 8-$OCHF_2$ | |
| 389 | $CH_3$ | $Q_2$ | 5-$OCF_2CHF_2$ | |
| 390 | $CH_3$ | $Q_2$ | 6-$OCF_2CHF_2$ | nD 1.5320 (26.2° C.) |
| 391 | $CH_3$ | $Q_2$ | 7-$OCF_2CHF_2$ | |
| 392 | $CH_3$ | $Q_2$ | 8-$OCF_2CHF_2$ | |
| 393 | $C_2H_5$ | $Q_2$ | 5-$OCF_2CHF_2$ | |
| 394 | $C_2H_5$ | $Q_2$ | 6-$OCF_2CHF_2$ | nD 1.5239 (26.7° C.) |
| 395 | $C_2H_5$ | $Q_2$ | 7-$OCF_2CHF_2$ | |
| 396 | $C_2H_5$ | $Q_2$ | 8-$OCF_2CHF_2$ | |
| 397 | $SO_2C_2H_5$ | $Q_2$ | 5-$OCF_2CHF_2$ | |
| 398 | $SO_2C_2H_5$ | $Q_2$ | 6-$OCF_2CHF_2$ | nD 1.5309 (26.0° C.) |
| 399 | $SO_2C_2H_5$ | $Q_2$ | 7-$OCF_2CHF_2$ | |
| 400 | $SO_2C_2H_5$ | $Q_2$ | 8-$OCF_2CHF_2$ | |
| 401 | $CH_2OCH_2$-Ph | $Q_2$ | 5-$OCF_2CHF_2$ | |
| 402 | $CH_2OCH_2$-Ph | $Q_2$ | 6-$OCF_2CHF_2$ | nD 1.5486 (26.2° C.) |
| 403 | $CH_2OCH_2$-Ph | $Q_2$ | 7-$OCF_2CHF_2$ | |
| 404 | $CH_2OCH_2$-Ph | $Q_2$ | 8-$OCF_2CHF_2$ | |
| 405 | $COOC_4H_9$-t | $Q_2$ | 5-$OCF_2CHF_2$ | |
| 406 | $COOC_4H_9$-t | $Q_2$ | 6-$OCF_2CHF_2$ | nD 1.5103 (26.2° C.) |
| 407 | $COOC_4H_9$-t | $Q_2$ | 7-$OCF_2CHF_2$ | |
| 408 | $COOC_4H_9$-t | $Q_2$ | 8-$OCF_2CHF_2$ | |
| 409 | $COCH_3$ | $Q_2$ | 5-$OCF_2CHF_2$ | |
| 410 | $COCH_3$ | $Q_2$ | 6-$OCF_2CHF_2$ | nD 1.5262 (25.8° C.) |
| 411 | $COCH_3$ | $Q_2$ | 7-$OCF_2CHF_2$ | |
| 412 | $COCH_3$ | $Q_2$ | 8-$OCF_2CHF_2$ | |
| 413 | $COC_2H_5$ | $Q_2$ | 5-$OCF_2CHF_2$ | |
| 414 | $COC_2H_5$ | $Q_2$ | 6-$OCF_2CHF_2$ | nD 1.5266 (25.9° C.) |
| 415 | $COC_2H_5$ | $Q_2$ | 7-$OCF_2CHF_2$ | |
| 416 | $COC_2H_5$ | $Q_2$ | 8-$OCF_2CHF_2$ | |
| 417 | $CH_2OCH_3$ | $Q_2$ | 5-$OCF_2CHF_2$ | |
| 418 | $CH_2OCH_3$ | $Q_2$ | 6-$OCF_2CHF_2$ | nD 1.5311 (23.9° C.) |
| 419 | $CH_2OCH_3$ | $Q_2$ | 7-$OCF_2CHF_2$ | |
| 420 | $CH_2OCH_3$ | $Q_2$ | 8-$OCF_2CHF_2$ | |
| 421 | $CH_2$-$Q_2$ | $Q_2$ | 5-$OCF_2CHF_2$ | |
| 422 | $CH_2$-$Q_2$ | $Q_2$ | 6-$OCF_2CHF_2$ | nD 1.5560 (26.8° C.) |
| 423 | $CH_2$-$Q_2$ | $Q_2$ | 7-$OCF_2CHF_2$ | |
| 424 | $CH_2$-$Q_2$ | $Q_2$ | 8-$OCF_2CHF_2$ | |
| 425 | $SO_2CH_3$ | $Q_2$ | 5-$C_3F_7$-i | |
| 426 | $SO_2CH_3$ | $Q_2$ | 6-$C_3F_7$-i | m.p. 154–156° C. |
| 427 | $SO_2CH_3$ | $Q_2$ | 7-$C_3F_7$-i | |
| 428 | $SO_2CH_3$ | $Q_2$ | 8-$C_3F_7$-i | |
| 429 | $SO_2C_2H_5$ | $Q_2$ | 5-$C_3F_7$-i | |
| 430 | $SO_2C_2H_5$ | $Q_2$ | 6-$C_3F_7$-i | m.p. 45–50° C. |
| 431 | $SO_2C_2H_5$ | $Q_2$ | 7-$C_3F_7$-i | |
| 432 | $SO_2C_2H_5$ | $Q_2$ | 8-$C_3F_7$-i | |
| 433 | $SO_2$(4-$CH_3$-Ph) | $Q_2$ | 5-$C_3F_7$-i | |
| 434 | $SO_2$(4-$CH_3$-Ph) | $Q_2$ | 6-$C_3F_7$-i | m.p. 65–75° C. |
| 435 | $SO_2$(4-$CH_3$-Ph) | $Q_2$ | 7-$C_3F_7$-i | |
| 436 | $SO_2$(4-$CH_3$-Ph) | $Q_2$ | 8-$C_3F_7$-i | |
| 437 | H | $Q_2$ | 6-$C_3F_7$-i | m.p. 186–21° C. (hydrochloride) |
| 438 | H | $Q_2$ | 6-$C_3F_7$-i | m.p. 168–208.8° C. (sulfate) |
| 439 | CO-Ph | $Q_2$ | 5-$C_3F_{7-i}$ | |
| 440 | CO-Ph | $Q_2$ | 6-$C_3F_{7-i}$ | m.p. 161–165° C. |
| 441 | CO-Ph | $Q_2$ | 7-$C_3F_{7-i}$ | |
| 442 | CO-Ph | $Q_2$ | 8-$C_3F_{7-i}$ | |
| 443 | $COC_3H_7$-i | $Q_2$ | 5-$C_3F_7$-i | |
| 444 | $COC_3H_7$-i | $Q_2$ | 6-$C_3F_7$-i | nD 1.5051 (22.1° C.) |
| 445 | $COC_3H_7$-i | $Q_2$ | 7-$C_3F_7$-i | |
| 446 | $COC_3H_7$-i | $Q_2$ | 8-$C_3F_7$-i | |
| 447 | $COCH_3$ | $Q_2$ | 5-$C_3F_7$-i | |
| 448 | $COCH_3$ | $Q_2$ | 6-$C_3F_7$-i | m.p. 132–134° C. |
| 449 | $COCH_3$ | $Q_2$ | 7-$C_3F_7$-i | |
| 450 | $COCH_3$ | $Q_2$ | 8-$C_3F_7$-i | |
| 451 | $COC_2H_5$ | $Q_2$ | 5-$C_3F_7$-i | |
| 452 | $COC_2H_5$ | $Q_2$ | 6-$C_3F_7$-i | m.p. 108° C. |
| 453 | $COC_2H_5$ | $Q_2$ | 7-$C_3F_7$-i | |
| 454 | $COC_2H_5$ | $Q_2$ | 8-$C_3F_7$-i | |
| 455 | $COC_3H_{7-n}$ | $Q_2$ | 5-$C_3F_7$-i | |
| 456 | $COC_3H_{7-n}$ | $Q_2$ | 6-$C_3F_7$-i | nD 1.510 (22.2° C.) |
| 457 | $COC_3H_{7-n}$ | $Q_2$ | 7-$C_3F_7$-i | |
| 458 | $COC_3H_{7-n}$ | $Q_2$ | 8-$C_3F_7$-i | |
| 459 | $CH_3$ | $Q_2$ | 5-$C_3F_7$-i | |
| 460 | $CH_3$ | $Q_2$ | 6-$C_3F_7$-i | m.p. 67–75° C. |
| 461 | $CH_3$ | $Q_2$ | 7-$C_3F_7$-i | |
| 462 | $CH_3$ | $Q_2$ | 8-$C_3F_7$-i | |
| 463 | $C_2H_5$ | $Q_2$ | 5-$C_3F_7$-i | |
| 464 | $C_2H_5$ | $Q_2$ | 6-$C_3F_7$-i | m.p. 98-102.4° C. |
| 465 | $C_2H_5$ | $Q_2$ | 7-$C_3F_7$-i | |
| 466 | $C_2H_5$ | $Q_2$ | 8-$C_3F_7$-i | |
| 467 | $COC_2H_5$ | $Q_2$ | 5-F | |
| 468 | $COC_2H_5$ | $Q_2$ | 6-F | nD 1.5660 (22.8° C.) |
| 469 | $COC_2H_5$ | $Q_2$ | 7-F | |
| 470 | $COC_2H_5$ | $Q_2$ | 8-F | |
| 471 | H | $Q_2$ | 5-$COOC_2H_5$ | |
| 472 | H | $Q_2$ | 6-$COOC_2H_5$ | m.p. 168.7–171.9° C. |
| 473 | H | $Q_2$ | 7-$COOC_2H_5$ | |
| 474 | H | $Q_2$ | 8-$COOC_2H_5$ | |
| 475 | $COC_2H_5$ | $Q_2$ | 5-$CF_3$ | |
| 476 | $COC_2H_5$ | $Q_2$ | 6-$CF_3$ | nD 1.5400 (21.1° C.) |
| 477 | $COC_2H_5$ | $Q_2$ | 7-$CF_3$ | |
| 478 | $COC_2H_5$ | $Q_2$ | 8-$CF_3$ | |
| 479 | H | $Q_2$ | 5-$C_2F_5$ | |
| 480 | H | $Q_2$ | 6-$C_2F_5$ | m.p. 139–146° C. |
| 481 | H | $Q_2$ | 7-$C_2F_5$ | |
| 482 | H | $Q_2$ | 8-$C_2F_5$ | |
| 483 | H | $Q_2$ | 6-Cl-7-$OCHF_2$ | m.p. 198–201° C. |
| 484 | $CH_2$≡CH | $Q_2$ | 6-$C_3F_7$-i | m.p. 96.1–101.3° C. |
| 485 | $CH_2OCH_3$ | $Q_2$ | 6-$C_3F_7$-i | nD 1.5163 (23.3° C.) |
| 486 | $CH_2SCH_3$ | $Q_2$ | 6-$C_3F_7$-i | nD 1.5211 (23.3° C.) |
| 487 | $CH_2CN$ | $Q_2$ | 6-$C_3F_7$-i | m.p. 109–113.1° C. |
| 488 | $CH_2$(3-Cl-Ph) | $Q_2$ | 6-$C_3F_7$-i | nD 1.5329 (20.6° C.) |
| 489 | $COCH_2Br$ | $Q_2$ | 6-$C_3F_7$-i | nD 1.4910 (23.5° C.) |
| 490 | $COCH_2OCH_3$ | $Q_2$ | 6-$C_3F_7$-i | nD 1.5106 (21.6° C.) |
| 491 | CO(3-Cl-Ph) | $Q_2$ | 6-$C_3F_7$-i | m.p. 54–58° C. |
| 492 | $COOC_2H_5$ | $Q_2$ | 6-$C_3F_7$-i | m.p. 140–148.3° C. |

TABLE 4-continued ($R^2$ = H, Y = O and $R^3$ = H, except for the group noted specially.)

| No | R | $R^1$ | Xn | Physical property |
|---|---|---|---|---|
| 493 | COOC$_4$H$_9$-t | Q$_2$ | 6-C$_3$F$_7$-i | nD 1.5598 (23.4° C.) |
| 494 | COOCH$_3$ | Q$_2$ | 6-C$_3$F$_7$-i | m.p. 130–135° C. |
| 495 | H | Q$_2$ | 6-OCH(CF$_3$)$_2$ | m.p. 137.5–139.9° C. |
| 496 | COC$_2$H$_5$ | Q$_2$ | 6-OCH(CF$_3$)$_2$ | nD 1.4932 (23.4° C.) |
| 497 | H | Q$_2$ | 6-CF$_2$CHFOCF$_2$ | m.p. 119.8–119.9° C. |
| 498 | COCH$_3$ | Q$_2$ | 6-CF$_2$CHFOCF$_2$ | nD 1.4977 (21.3° C.) |
| 499 | COC$_2$H$_5$ | Q$_2$ | 6-CF$_2$CHFOCF$_2$ | nD 1.5000 (24.4° C.) |
| 500 | H | Q$_2$ | 6-O-(3-CF$_3$-Ph) | m.p. 113.8–116.0° C. |
| 501 | H | Q$_2$ | 6-O-(3-Cl-5-CF$_3$-2-Pyr) | m.p. 75–81° C. |

EXAMPLES

Typical examples of the present invention are described below, however the scope of the present invention is not restricted by said examples.

Example 1

Preparation of 3-amino-3,4-dihydro-6-trifluoro-methoxy-2-(1H)-quinazolinone (Compound No. II-30)

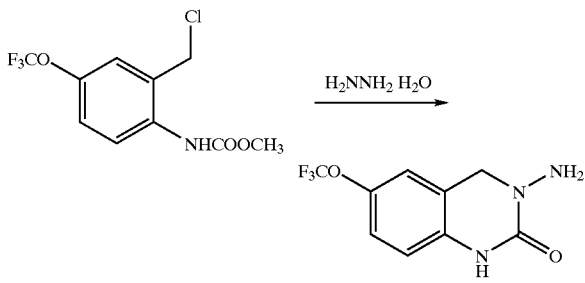

In 20 ml of methanol was dissolved 2.84 g (0.01 mole) of methyl 2-chloromethyl-4-trifluoro-methoxyphenylcarbamate, then 5 g (0.1 mole) of hydrazine hydrate was added to the solution, and the reaction was conducted by heating under reflux for 3 hours.

After completion of the reaction, the remainder of hydrazine hydrate and the solvent were removed from the reaction mixture containing the desired compound by distillation under reduced pressure to obtain a crude product. The resulting crude product was recrystallized from 95% methanol to obtain 2.22 g of the desired compound.

Physical property: m.p. 181.5–184° C.

Yield: 90%.

Example 2

Preparation of 3-amino-3,4-dihydro-6-pentafluoro-ethyl-2-(1H)-quinazolinone (Compound No. II-18)

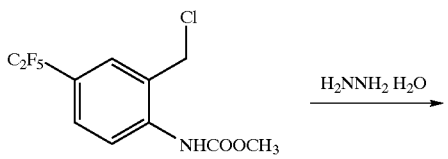

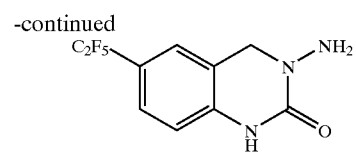

In 20 ml of methanol was dissolved 3.18 g (0.01 mole) of methyl 2-chloromethyl-4-pentafluoro-ethylphenylcarbamate, then 5 g (0.1 mole) of hydrazine hydrate was added to this solution and the reaction was conducted by heating under reflux for 3 hours.

After completion of the reaction, the remainder of hydrazine hydrate and the solvent were removed from the reaction mixture containing the desired compound by distillation under reduced pressure to obtain a crude product. The resulting crude product was recrystallized from 95% methanol to obtain 2.53 g of the desired compound.

Physical property: m.p. 178.4–183.5° C.

Yield: 90%.

Example 3

Preparation of 3-(3-pyridylmethylideneamino)-3,4-dihydro-6-trifluoromethoxy-2(1H)-quinazolinone (Compound No. 30)

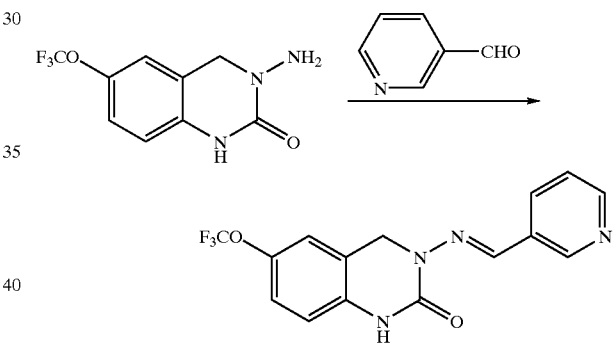

To 10 ml of methanol were added 0.62 g (2.5 mmoles) of 3-amino-3,4-dihydro-6-trifluoromethoxy-2(1H)-quinazolinone, 0.27 g (2.5 mmole) of nicotinaldehyde and 1 drop of sulfuric acid, then the reaction was conducted by heating under reflux for 3 hours.

After completion of the reaction, the crystals precipitated in the reaction system were collected by filtration and dried to obtain 0.76 g of the desired product.

Physical property: m.p. 264.5–266.0° C.

Yield: 93%.

Example 4

Preparation of 3-[1-(3-pyridylmethideneamino)-3,4-dihydro-6-pentafluoroethyl-2(1H)-quinazolinone (Compound No. 18)

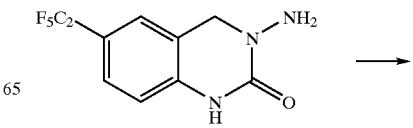

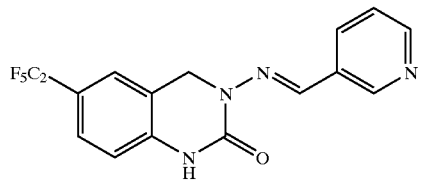

To 10 ml of methanol were added 0.74 g (2.5 mmols) of 3-amino-3,4-dihydro-6-pentafluoroethyl-2(1H)-quinazolinone, 0.27 g (2.5 mmols) of nicotinaldehyde and 1 drop of sulfuric acid, then the reaction was conducted by heating under reflux for 3 hours.

After completion of the reaction, the crystals precipitated in the reaction system were collected by filtration and dried to obtain 0.78 g of the desired product.

Physical property: m.p. 298.0–300.0° C.

Yield: 84%.

Example 5

Preparation of 3-(3-pyridylmethylamino)-3,4-dihydro-6-trifluoromethoxy-2(1H)-quinazolinone (Compound No. 208)

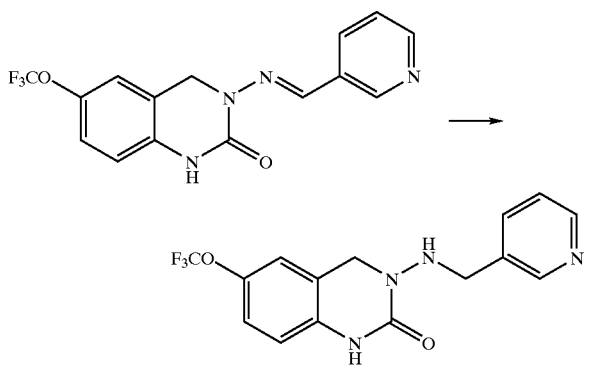

To 30 ml of acetic acid were added 3.36 g (2.5 mmols) of 3-(3-pyridylmethylideneamino)3,4-dihydro-6-trifluoromethoxy-2(1 H)-quinazolinone and 0.2 g of 5% palladium-carbon, then the hydrogenation was conducted at 3 to 4 kg/cm².

After the absorption of a theoretical amount of hydrogen, the catalyst was removed from the reaction mixture by filtration, and the solvent was removed by distillation under reduced pressure. The residue was neutralized by adding a 20% aqueous sodium hydroxide solution and the desired compound was extracted with chloroform (20 ml×3). The extracted solution was washed with water and an aqueous solution saturated with sodium chloride, dried over anhydrous magnesium sulfate, the solvent was removed by distillation under reduced pressure. The resulting crude product was purified by a silica gel column chromatography (ethyl acetate-methanol=10:1) to obtain 2.5 g of the desired compound.

Physical property: nD 1.5233 (22.6° C.).

Yield: 74%.

Example 6

Preparation of 1-methyl-3-(3-pyridylmethylamino)-3,4-dihydro-6-trifluoromethoxy-2(1H)-quinazolinone (Compound No. 289)

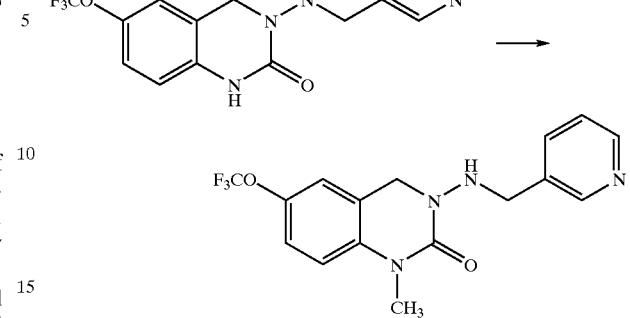

In 10 ml of dimethylformamide was dissolved 0.68 g (2.0 mmols) of 3-(3-pyridylmethylamino)-3,4-dihydro-6-trifluoromethoxy-2(1H)-quinazolinone. To the solution, 0.09 g of sodium hydride (62.4%) was added, and the reaction was conducted at room temperature for 30 minutes, then 0.34 g of methyl iodide was added thereto and the reaction was conducted for 4 hours.

After completion of the reaction, the reaction mixture was poured into an ice-water, the desired compound was extracted with ethyl acetate (20 ml×3). The extracted solution was washed with water and saturated aqueous sodium chloride, dried over anhydrous magnesium sulfate, and the solvent was removed by distillation under reduced pressure. The resulting crude product was purified by a silica gel column chromatography (ethyl acetate-methanol=10:1) to obtain 2.5 g of the desired compound.

Physical property: nD 1.5467 (23° C.).

Yield: 50%.

Example 7

7-1. Preparation of t-butyl 2-(5-hydroxy-2-nitrophenylmethylidene)carbazate

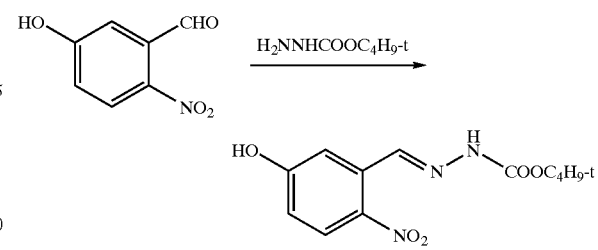

To 20 ml of methanol were added 3.34 g (0.02 mole) of 5-hydroxy-2-nitrobenzaldehyde, 2.64 g (0.02 mole) of t-butyl carbazate and 1 drop of sulfuric acid, and the reaction was conducted by heating under reflux for 3 hours.

After completion of the reaction, the reaction mixture was cooled to room temperature, the crystals precipitated were collected by filtration to obtain 5.06 g of the desired compound.

$^1$H-NMR [CDCl$_3$/TMS, δ(ppm)] 1.57 (9H, s), 6.84 (1H, d.d), 7.66 (1H, d), 7.94 (1H, d), 8.42 (1H, br.s), 8.46 (1H, s), 10.5 (1H, br. s).

Yield: 90%.

7-2. Preparation of t-butyl 2-(5-methoxycarbonyloxy-2-nitrophenylmethylidene)carbazate

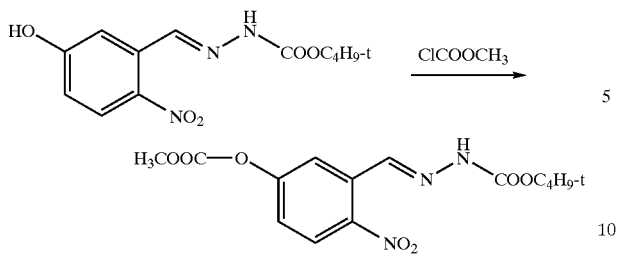

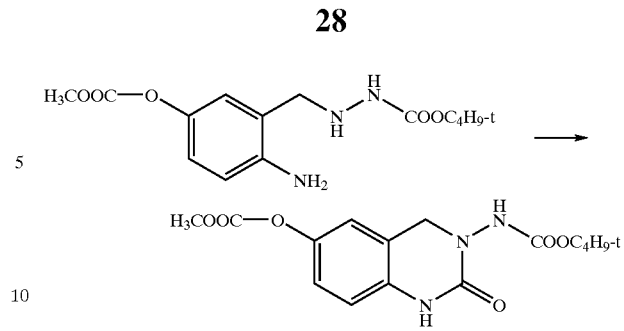

In 15 ml of tetrahydrofuran were dissolved 4.22 g (0.015 mole) of t-butyl 2-(5-hydroxy-2-nitrophenyl-methylidene) carbazate obtained in Example 7-1 and 1.67 g (0.0165 mole) of triethylamine, then the solution was cooled to 0° C. By taking 15 minutes, to the solution was added dropwise 1.56 g (0.0165 mole) of methyl chlorofomate dissolved in 5 ml of tetrahydro-furan, then the reaction was continued at room temperature for 3 hours. After completion of the reaction, the reaction mixture was poured into 20 ml of water, and the desired compound was extracted with ethyl acetate (20 ml×3). The extracted solution was washed with water and saturated aqueous sodium chloride, dried over anhydrous magnesium sulfate, then the solvent was removed by distillation under reduced pressure. The resulting crude product was recrystallized from hexane-ether to obtain 4.6 g of the desired compound.

$^1$H-NMR [(CDCl$_3$/TMS, δ(ppm)] 1.54 (9H, s), 3.93 (3H, s), 7.33 (1H, d.d), 8.06 (1H, d), 8.14 (1H, d), 8.21 (1H, br.s), 8.45 (1H, s).

Yield: 90%.

7-3. Preparation of t-butyl 2-(2-amino-5-methoxycarbonyloxyphenylmethyl)carbazate

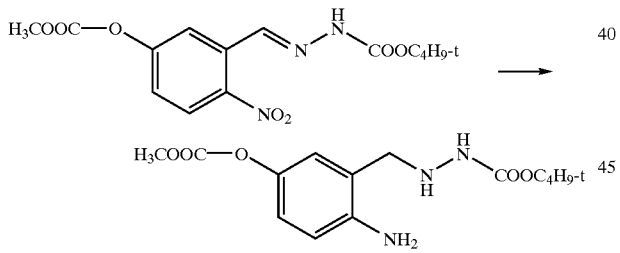

To 50 ml of methanol were added 4.4 g (0.013 mole) of t-butyl 2-(5-methoxycarbonyloxy-2-nitrophenyl-methylidene)carbazate obtained in Example 7-2 and 0.4 g of 5% palladium-carbon, then the catalytic reduction was conducted at 3-4 kg/cm$^2$.

After the absorption of a theoretical amount of hydrogen, the catalyst was removed from the reaction mixture by filtration, and the solvent was removed by distillation under reduced pressure, to obtain 4 g of the desired compound.

$^1$H-NMR [(CDCl$_3$/TMS, δ(ppm)] 1.46 (9H, s), 3.87 (3H, s), 3.96 (2H, d), 4.6–5.0 (3H, br.s.), 6.05 (1H, br.s), 6.6–6.7 (1H, m), 6.8–7.0 (2H, m).

Yield: Quantitative.

7-4. Preparation of 3-t-butoxycarbonylamino-6-methoxy-carbonyloxy-3,4-dihydro-2(1H)-quinazolinone In 20 ml of tetrahydrofuran were dissolved 3.1 g (0.01 mole) of t-butyl 2-(2-amino-5-methoxycarbonyloxyphenylmethyl)carbazate obtained in Example 7-3 and 2.6 g (0.01 mole) of 1,1'-carbonyl-bis(1H-imidazole), the reaction was conducted at room temperature for 3 hours.

After completion of the reaction, the reaction mixture was poured into 20 ml of water, and the desired compound was extracted with ethyl acetate (20 ml×3). The extracted solution was washed with water and saturated aqueous sodium chloride, dried over anhydrous magnesium sulfate, and the solvent was removed by distillation under reduced pressure. The crude product thus obtained was recrystallized from hexane-ethyl acetate, 2.1 g of the desired compound was obtained.

$^1$-H-NMR [DMSO-d$_6$/TMS, δ(ppm)] 1.42 (9H, s), 3.80 (3H, s), 4.81 (2H, s), 6.5–6.7 (3H, m), 9.01 (1H, s), 9.15 (1H, br.s).

Yield: 60%.

7-5. Preparation of 3-t-butoxycarbonylamino-6-hydroxy-3,4-dihydro-2(1H)-quinazolinone

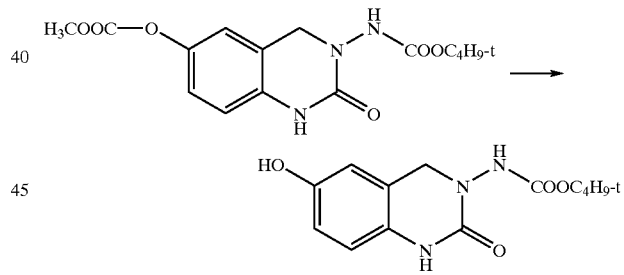

To 20 ml of 50% methanol were added 2.1 g (0.0062 mole) of 3-t-butoxycarbonylamino-6-methoxycarbonyloxy-3,4-dihydro-2(1H)-quinazolinone obtained in Example 7-4 and 0.64 g (0.0063 mole) of sodium carbonate, then the reaction was conducted by heating under reflux for 3 hours.

After completion of the reaction, the methanol was removed by distillation under reduced pressure. To the residue thus obtained was added 10 ml of water and was collected by filtration, then recrystallization from 95% methanol to obtain 1.3 g of the desired compound.

$^1$H-NMR [DMSO-d$_6$/TMS, δ(ppm)] 1.42 (9H, s), 4.81 (2H, s), 6.5–6.7 (3H, s), 9.01 (1H, s), 9.10 (1H, s), 9.15 (1H, br.s).

Yield: 75%.

7-6. Preparation of 3-amino-6-hydroxy-3,4-dihydro-2(1H)-quinazolinone (Compound No. II-2)

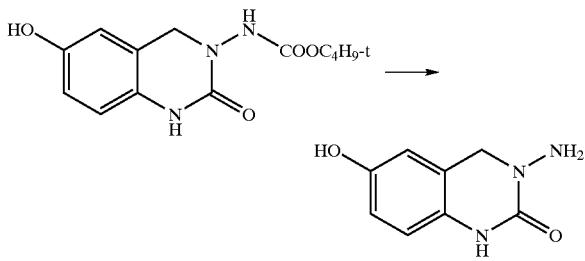

To 20 ml of trifluoroacetic acid was added 1.3 g (0.0046 mole) of 3-t-butoxycarbonylamino-6-hydroxy-3,4-dihydro-2(1H)-quinazolinone obtained in Example 7-5, then the reaction was conducted at room temperature for 3 hours.

After completion of the reaction, 10 ml of methanol was added to the reaction mixture, the solvent was removed by distillation under reduced pressure. The resulting residue was recrystallized from methanol to obtain 0.74 g of the desired compound.

$^1$H-NMR [DMSO-$d_6$/TMS, δ(ppm)] 4.95 (2H, s), 4.65 (2H, s), 6.51–6.63 (3H, m), 9.00 (1H, s), 9.60 (1H, br.s).

Yield: 90%.

Pest controllers containing, as an active ingredient, the substituted aminoquinazolinone (thione) derivative of the general formula (I) or salt thereof of the present invention are suitable for controlling various insect pests such as agricultural insect pests, forest insect pests, horticultural insect pests, stored grain insect pests, sanitary insect pests, nematodes, etc. They have an insecticidal effect also, for example, on HEMIPTERA including tea green leafhopper (*Empoasca onukii*), green rice leafhopper (*Nephotettix cincticeps*), brown rice planthopper (*Nilaparvata lugens*), whitebacked rice planthopper (*Sogatella furcifera*), citrus psylla (*Diaphorina citri*), citrus whitefly (*Dialeurodes citri*), sweetpotato whitefly (*Bemisia tabaci*), greenhouse whitefly (*Trialeurodes vaporariorum*), Cabbage aphid (*Brevicoryne brassicae*), Cotton aphid (*Aphis gossypii*), Wheat aphid (*Rhopalosiphum padi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis yanonensis*), rice leaf bug (*Trigonotylus colelestialium*), etc., TYLENCHIDA including coffee root-lesion nematode (*Pratylenchus coffeae*), potato cyst nematode (*Globodera rostochiensis*), root-knot nematode (*Meloidogyne sp.*), citrus nematode (*Tylenchulus semipenetrans*), Aphelenchus sp. (*Aphelenchus avenae*) chrysanthemum foliar nematode (*Aphelenchoides ritzemabosi*), etc., and ORTHOPTERA including rice thrips (*Stenchaetothrips biformis*), etc.

The zoological names and the like are in accordance with Applied Zoology and Entomology Society of Japan, "List of Agricultural and Forest Injurious Animals and Insects", published in 1987.

The pest controller containing as an active ingredient the substituted aminoquinazolinone (thione) derivative of the general formula (I) or salt thereof of the present invention has a marked control effect on the above-exemplified insect pests, sanitary pests, and/or nematodes, which are injurious to paddy fields, fruit trees, vegetables and other crops, and flowers and ornamental plants. Therefore, the desired effect of the insecticide of the present invention can be obtained by applying the insecticide to the paddy field water, paddy-rice plant, fruit trees, vegetables, other crops, seeds of flowers and ornamental plants, roots, stalks and leaves of plants, soil, etc., or to the inside of a house or ditches around a house, in which the above-exemplified sanitary insect pests injurious to men and beasts appear or are expected to appear. The application is carried out at a season at which the insect pests, sanitary pests or nematodes are expected to appear, before their appearance or at the time when their appearance is confirmed. The present invention however should not be limited to these embodiment.

When the substituted aminoquinazolinone (thione) derivative of the general formula (I) or salt thereof of the present invention is used as a pest controller, the derivative or salt is generally prepared into conveniently usable forms according to an ordinary manner for preparation of agrochemicals.

That is, the substituted aminoquinazolinone (thione) derivative of the general formula (I) or salt thereof of the present invention and, optionally, an adjuvant are blended with a suitable inert carrier in a proper proportion and prepared into a suitable preparation form such as a suspension, emulsifiable concentrate, soluble concentrate, wettable powder, granules, dust or tablets through dissolution, dispersion, suspension, mixing, impregnation, adsorption or sticking.

The inert carrier used in the present invention may be either solid or liquid. As the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, i.e. synthetic, high-dispersion silicic acid, also called finely divided hydrated silica or hydrated silicic acid, some of commercially available products contain calcium silicate as the major component), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform and carbon tetrachloride; esters such as ethyl cetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicon oils may also be used as a defoaming agent.

The content of the active ingredient may be varied as required. In dusts or granules, the suitable content thereof is from 0.01 to 50% by weight. In emulsifiable concentrates or flowable wettable powders, it is also from 0.01 to 50% by weight.

The pest controller containing as an active ingredient the substituted aminoquinazolinone (thione) derivative of the general formula (I) or salt thereof of the present invention is used to control a variety of insect pests in the following manner. That is, it is applied to the insect pests or a site where appearance or growth of the insect pests is undesirable, as it is or after being properly diluted with or suspended in water or the like, in an amount effective for control of the insect pests.

The applying dosage of the pest controller containing as an active ingredient the substituted aminoquinazolinone (thione) derivative of the general formula (I) or salt thereof of the present invention is varied depending upon various factors such as a purpose, insect pests to be controlled, a growth state of a plant, tendency of insect pests appearance, weather, environmental conditions, a preparation form, an application method, an application site and application time. It may be properly chosen in the range of 0.1 g to 5 kg (in terms of the active ingredient) per 10 ares depending upon purposes.

The pest controller containing as an active ingredient the substituted aminoquinazolinone (thione) derivative of the general formula (I) or salt thereof of the present invention may be used in admixture with other insecticides or fungicides in order to expand both spectrum of controllable insect pest species and the period of time when effective applications are possible or to reduce the dosage.

Typical formulation examples and test examples of the present invention are described below but they should not be construed as limiting the scope of the invention.

In the formulation examples, parts are all by weight.

Formulation Example 1

| | |
|---|---|
| Each compound listed in Tables 3 and 4 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Tables 3 and 4 | 3 parts |
| Clay powder | 82 parts |
| Diatomaceous earch powder | 15 parts |

A dust was prepared by mixing uniformly and grinding the above ingredients.

Formulation Example 3

| | |
|---|---|
| Each compound listed in Tables 3 and 4 | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 3 and 4 | 20 parts |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Control Efficacy Against Green Peach Aphid (*Myzus persicae*)

A Chinese cabbage plant was planted in each of plastic pots with a diameter of 8 cm and a height of 8 cm and green peach aphids were propagated on the plant, after which the parasites in each pot were counted.

Each substituted aminoquinazolinone (thione) derivative of the general formula (I) or salt thereof of the present invention listed in Tables 3 and 4 was dispersed in and diluted with water to obtain a 500 ppm liquid chemical. The stalks and leaves of the potted Chinese cabbage plants were sprayed with the liquid chemical and air-dried, and then the pots were stored in a greenhouse. Six days after the spraying, green peach aphids parasitic on each Chinese cabbage plant were counted and the control efficacy degree was calculated by the following equation, whereby the insecticidal effect was judged according to the criterion shown below.

$$\text{Control efficacy} = 100 - \{(T \times Ca)/(Ta \times C)\} \times 100$$

Ta: number of parasites before spraying in treated group,
T: number of parasites after spraying in treated group, Ca: number of parasites before spraying in untreated group,
C: number of parasites after spraying in untreated group.
Criterion:

| Efficacy | Percent Control (%) |
|---|---|
| A | 100 |
| B | 99–90 |
| C | 89–80 |
| D | 79–50 |

Test Example 2
Insecticidal Effect on Brown Rice Planthopper (*Nilaparvata lugens*)

Each substituted aminoquinazolinone (thione) derivative of the general formula (I) or salt thereof of the present invention listed in Tables 3 and 4 was dispersed in and diluted with water to obtain a 500 ppm liquid chemical. Rice seedlings (cultivar: Nihonbare) were immersed in the liquid chemical for 30 seconds and air-dried, after which each seedling was placed in a glass test tube and inoculated with 10 third-instar nymphs of brown rice planthopper, and the test tube was pluged with a cotton plug. Eight days after the inoculation, the dead and alive were counted. The mortality was calculated by the following equation and the control effect was judged according to the criterion described below.

Corrected larval mortality (%)={(Ca/c−Ta/T)/Ca/c}×100

Ta: number of alive nymphs in treated groups
T: number of inoculated nymphs in treated groups
Ca: number of alive numphs in untreated groups
c: number of inoculated nymphs in untreated groups
Criterion: the same as in Test Example 1.

Test Example 3
Insecticidal Test on Greenhouse Whitefly (*Trialeurodes vaporariorum*)

Each compounds of the present invention listed in Table 3 and Table 4 was dispersed in and diluted with water to prepare a test liquid containing 100 ppm of the test compound. By use of a spraygun, the test liquid was sprayed on the surface of a leaf of tomato plant put in a 20 ml-vial bottle containing water on a turn table. After air-dried, the leaf treated with the test liquid was put in a glass cylinder, and inoculated with 20 adults of greenhouse whitefly thereon. After the inoculation, the leaf was placed in a greenhouse, and the number of adults of greenhouse whitefly was counted. The mortality of the adults was calculated similar to that of conducted in Test Example 2, and the insecticidal effect of each one of the test compounds was evaluated by the method identical to Test Example 1.

From the results obtained in Test Example 1, 2 and 3 that: in Test Example 1, Compound Nos. 6, 18, 22, 26, 30, 184, 200, 204 and 208 showed excellent insecticidal effect rated A against green peach aphid (*Myzus persicae*); in Test Example 2, Compound Nos. 6, 18, 22, 26, 30, 184, 200, 204 and 208 showed excellent insecticidal effect rated A against planthopper (*Nilaparvata lugens*); and in Test Example 3, Compound Nos. 6, 10, 14, 18, 22, 26, 30, 38, 78, 86, 90, 184, 200, 204 and 208 showed excellent insecticidal effect rated D or higher against greenhouse whitefly (*Trialeurodes vaporariorum*); particularly, Compound Nos. 6, 18, 22, 26, 30, 184, 200, 204 and 208 showed excellent insecticidal effect rated A.

What is claimed is:
1. A substituted aminoquinazolinone (thione) derivative represented by the general formula (I), or a salt thereof:

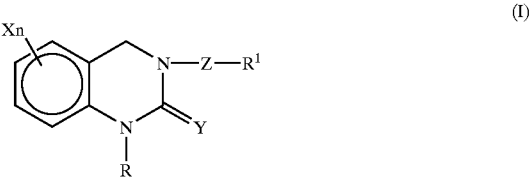

wherein R is a hydrogen atom; a hydroxyl group; a formyl group; a $(C_{1-12})$alkyl group; a halo$(C_{1-6})$alkyl group; a hydroxy $(C_{1-6})$ alkyl group; a $(C_{2-6})$ alkenyl group; a $(C_{2-6})$alkynyl group; a $(C_{1-6})$alkoxy group; a halo$(C_{1-6})$ alkoxy group; a $(C_{1-6})$alkoxy $(C_{1-3})$alkyl group; a $(C_{1-6})$-alkoxy $(C_{1-3})$ alkoxy $(C_{1-3})$ alkyl group; a $(C_{1-6})$ alkylthio group; a halo$(C_{1-6})$alkylthio group; a $(C_{1-6})$alkylsulfinyl group; a $(C_{1-6})$alkylsulfonyl group; a $(C_{1-6})$alkylthio$(C_{1-3})$ alkyl group; a di$(C_{1-6})$alkoxy$(C_{1-3})$alkyl group in which the $(C_{1-6})$alkoxy groups may be the same or different; an unsubstituted amino$(C_{1-6})$alkyl group; a substituted amino$(C_{1-6})$ alkyl group having one or two substituents which may be the same or different and are selected from the group consisting of $(C_{1-6})$alkyl groups, halo$(C_{1-6})$alkyl groups, $(C_{2-6})$alkenyl groups and $(C_{2-6})$alkynyl groups; a cyano$(C_{1-6})$alkyl group; a $(C_{1-6})$alkylcarbonyl group; a $(C_{1-6})$alkoxycarbonyl group; a hydroxycarbonyl-$(C_{1-3})$ alkyl group; a $(C_{1-6})$ alkoxycarbonyl $(C_{1-3})$ alkyl group; an unsubstituted aminocarbonyl group; a substituted aminocarbonyl group having one or two substituents which may be the same or different and are selected from the group consisting of $(C_{1-6})$alkyl groups, $(C_{2-6})$-alkenyl groups and $(C_{2-6})$alkynyl groups; a $(C_{3-6})$-cycloalkyl $(C_{1-3})$alkyl group; an unsubstituted phenyl$(C_{1-3})$ alkyl group; a substituted phenyl$(C_{1-3})$alkyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$alkoxy groups, halo $(C_{1-6})$alkoxy groups, $(C_{1-6})$alkylthio groups and halo $(C_{1-6})$ alkylthio groups; an unsubstituted phenylcarbonyl group; a substituted phenylcarbonyl group having on the ring 1 to 5 substituents which may be the same or different and are selected from the group consisting of halogen atoms, nitro groups, cyano groups, $(C_{1-6})$alkyl groups, halo$(C_{1-6})$alkyl groups, $(C_{1-6})$-alkoxy groups, halo$(C_{1-6})$alkoxy groups, $(C_{1-6})$alkylthio groups and halo$(C_{16})$alkylthio groups; an unsubstituted phenylthio group; a substituted phenylthio group having on the ring 1 to 5 substituents which may be the same or different and are selected from the group consisting of halogen atoms, nitro groups, cyano groups, $(C_{1-6})$alkyl groups, halo$(C_{1-6})$ alkyl groups, $(C_{1-6})$alkoxy groups, halo$(C_{1-6})$alkoxy groups, halo$(C_{1-6})$alkoxy groups, $(C_{1-6})$alkylthio groups and halo$(C_{1-6})$alkylthio groups; an unsubstituted phenylsulfonyl group; a substituted phenylsulfonyl group having on the ring 1 to 5 substituents which may be the same or different and are selected from the group consisting of halogen atoms, nitro groups, cyano groups, $(C_{1-6})$alkyl groups, halo$(C_{1-6})$ alkyl groups, $(C_{1-6})$ alkoxy groups, halo$(C_{1-6})$alkoxy groups, $(C_{1-6})$alkylthio groups and halo $(C_{1-6})$ alkylthio groups; an unsubstituted phenyl $(C_{1-6})$alkylsulfonyl group; a substituted phenyl$(C_{1-6})$alkylsulfonyl group having on the ring 1 to 5 substituents which may be the same or different and are selected from the group consisting of halogen atoms, nitro groups, cyano groups, $(C_{1-6})$alkyl groups, halo$(C_{1-6})$ alkyl groups, $(C_{1-6})$alkoxy groups, halo$(C_{1-6})$alkoxy groups, $(C_{1-}$ ₆)alkylthio groups and halo($C_{1-6}$)alkylthio groups; an unsubstituted phenyloxycarbonyl group; a substituted phenyloxycarbonyl group having on the ring 1 to 5 substituents which may be the same or different and are selected from the group consisting of halogen atoms, nitro groups, cyano groups, ($C_{1-6}$)alkyl groups, halo($C_{1-6}$)alkyl groups, ($C_{1-6}$)alkoxy groups, halo ($C_{1-6}$)alkoxy groups, ($C_{1-6}$)alkylthio groups and halo($C_{1-6}$)-alkylthio groups; an unsubstituted phenyloxy($C_{1-3}$)alkyl group; a substituted phenyloxy($C_{1-3}$)alkyl group having on the ring 1 to 5 substituents which may be the same or different and are selected from the group consisting of halogen atoms, nitro groups, cyano groups, ($C_{1-6}$)alkyl groups, halo($C_{1-6}$)alkyl groups, ($C_{1-6}$)alkoxy groups, halo ($C_{1-6}$) alkoxy groups, ($C_{1-6}$)alkylthio groups and halo($C_{1-6}$) alkylthio groups; an unsubstituted phenyl($C_{2-6}$)-alkenyl group; a substituted phenyl ($C_{2-6}$)alkenyl group having on the ring 1 to 5 substituents which may be the same or different and are selected from the group consisting of halogen atoms, nitro groups, cyano groups, ($C_{1-6}$)alkyl groups, halo($C_{1-6}$)alkyl groups, ($C_{1-6}$)alkoxy groups, halo ($C_{1-6}$)alkoxy groups, ($C_{1-6}$)alkylthio groups, halo($C_{1-6}$)alkylthio groups and ($C_{1-2}$)alkylenedioxy groups; an unsubstituted phenyl($C_{2-6}$)alkynyl group; a substituted phenyl($C_{2-6}$)alkynyl group having on the ring 1 to 5 substituents which may be the same or different and are selected from the group consisting of halogen atoms, nitro groups, cyano groups, ($C_{1-6}$)alkyl groups, halo($C_{1-6}$)alkyl groups, ($C_{1-6}$)alkoxy groups, halo($C_{1-6}$)alkoxy groups, ($C_{1-6}$)alkylthio groups, halo($C_{1-6}$)alkylthio groups and ($C_{1-2}$)alkylenedioxy groups; an unsubstituted phenyl ($C_{2-4}$)alkynyl ($C_{1-3}$)alkyl group; a substituted phenyl ($C_{2-4}$)alkynyl ($C_{1-3}$)alkyl group having on the ring 1 to 5 substituents which may be the same or different and are selected from the group consisting of halogen atoms, nitro groups, cyano groups, ($C_{1-6}$)alkyl groups, halo($C_{1-6}$) alkyl groups, ($C_{1-6}$)alkoxy groups, halo ($C_{1-6}$) alkoxy groups, ($C_{1-6}$) alkylthio groups, halo ($C_{1-6}$) alkylthio groups and ($C_{1-2}$)alkylenedioxy groups; a 1,3-dioxolan-2-yl($C_{1-3}$)alkyl group; or a phthalimido($C_{1-6}$)alkyl group, $R^1$ is a 5- or 6-membered heterocyclic ring having 1 to 3 heteroatoms which may be the same or different and are selected from the group consisting of oxygen atom, sulfur atom and nitrogen atom, said heterocyclic ring may have 1 to 5 substituents which may be the same or different and are selected from the group consisting of halogen atoms, cyano groups, ($C_{1-6}$)alkyl groups, halo ($C_{1-6}$)alkyl groups and ($C_{1-6}$)alkoxy groups, and the nitrogen atom in the heterocyclic ring may form an N-oxide group, Y is an oxygen atom or a sulfur atom, Z is

—N($R^3$)—CH($R^2$)—

(wherein $R^2$ is a hydrogen atom, a ($C_{1-6}$)alkyl group or a halo($C_{1-6}$)alkyl group, and $R^3$ is a hydrogen atom, a ($C_{1-6}$) alkyl group, a formyl group, a ($C_{1-3}$)-alkylcarbonyl group or a halo($C_{1-3}$)alkylcarbonyl group), X may be the same or different, and is a halo($C_{1-10}$)alkyl group; and n is an integer of 1 to 4.

2. A composition comprising as an active ingredient a substituted aminoquinazolinone (thione) derivative or a salt thereof set forth in claim 1.

3. A method for controlling pests which comprises applying a composition comprising as an active ingredient a substituted aminoquinazolinone (thione) derivative or a salt thereof set forth in claim 1, to objective crops or soil.

* * * * *